United States Patent
Moszner et al.

(10) Patent No.: US 11,198,668 B2
(45) Date of Patent: Dec. 14, 2021

(54) POLYMER MATERIALS WITH UNSATURATED TRANSFER REAGENTS

(71) Applicants: Ivoclar Vivadent AG, Schaan (LI); Technische Universität Wien, Vienna (AT)

(72) Inventors: Norbert Moszner, Triesen (LI); Yohann Catel, Rans (CH); Iris Lamparth, Grabs (CH); Robert Liska, Schleinbach (AT); Christian Gorsche, Vienna (AT); Gernot Peer, Vienna (AT)

(73) Assignees: Ivoclar Vivadent AG, Schaan (LI); Technische Universität Wien, Vienna (AT)

( * ) Notice: Subject to any disclaimer, the term of this patent is extended or adjusted under 35 U.S.C. 154(b) by 170 days.

(21) Appl. No.: 16/545,138

(22) Filed: Aug. 20, 2019

(65) Prior Publication Data

US 2020/0087241 A1 Mar. 19, 2020

(30) Foreign Application Priority Data

Sep. 17, 2018 (EP) .................................... 18194789

(51) Int. Cl.

| | |
|---|---|
| *C08F 2/46* | (2006.01) |
| *C08F 2/50* | (2006.01) |
| *C08G 61/04* | (2006.01) |
| *C07C 69/734* | (2006.01) |
| *A61L 27/16* | (2006.01) |
| *C08F 222/20* | (2006.01) |
| *A61K 6/889* | (2020.01) |

(52) U.S. Cl.
CPC ............ *C07C 69/734* (2013.01); *A61K 6/889* (2020.01); *A61L 27/16* (2013.01); *C08F 222/20* (2013.01)

(58) Field of Classification Search
CPC ....... A61K 6/887; A61K 6/889; C08F 222/20; C08L 33/10; C07C 69/734; A61L 27/16
USPC .................................. 522/181, 178, 1; 520/1
See application file for complete search history.

(56) References Cited

U.S. PATENT DOCUMENTS

| | | | |
|---|---|---|---|
| 2,694,699 A | 11/1954 | Laakso et al. | |
| 5,932,675 A | 8/1999 | Rizzardo et al. | |
| 9,320,685 B2 | 4/2016 | Moser et al. | |
| 10,342,744 B2 | 7/2019 | Moszner et al. | |
| 2017/0172855 A1* | 6/2017 | Moszner | ............... C07C 323/52 |
| 2018/0369075 A1 | 12/2018 | Moszner et al. | |

FOREIGN PATENT DOCUMENTS

| | | | |
|---|---|---|---|
| WO | 8804304 A1 | 6/1988 | |
| WO | WO-2016005534 A1 * | 1/2016 | ............. A61K 6/887 |

OTHER PUBLICATIONS

Shah et al., Application of an addition-fragmentation-chain transfer monomer in di(meth)acrylate network formation to reduce polymerization shrinkage stress, Jun. 21, 2017, Polym. Chem. (Year: 2017).*
Elias, "Radical Polymerizations," Macromolecules, pp. 299-352, Wiley-VCH, Weinhem etc., 1999.
Moad, et al., "Chain Transfer Activity of w-Unsaturated Methyl Methacrylate Oligomers," Macromolecules, 29, pp. 7717-7726, 1996.
Deguest, G. et al., "Anionic, In Situ Generation of Formaldehyde: A Very Useful and Versatile Tool in Synthesis," Organic Letters, vol. 9, No. 6, pp. 1165-1167, 2007.
Rehbein, J. et al., "Gosteli—Claisen Rearrangement: Substrate Synthesis, Simple Diastereoselectivity, and Kinetic Studies," Article, J. Org. Chem., 74, pp. 1531-1540, 2009.
Shah, Parag K. et al., "Application of an addition-fragmentation-chain transfer monomer in di(meth)acrylate network formation to reduce polymerization shrinkage stress," The Royal Society of Chemistry, Polymer Chemistry, 13 pages, 2017.
Watts, D.C. et al., "Photo-polymerization shrinkage-stress kinetics in resin-composites: methods development," Academy of Dental Materials, vol. 19, pp. 1-11, 2003.
Moad, G. et al., "Radical addition-fragmentation chemistry in polymer synthesis," ScienceDirect, Elsevier Ltd., Polymer 49 (2008) 1079-1131.
Meijs, G. et al., "The use of activated benzyl vinyl ethers to control molecular weight in free radical polymerizations," Makromol. Chem., 191, 1545-1553, 191 (1990).
Shah, Parag K. et al., "Application of an addition-fragmentation-chain transfer monomer in de(meth)acrylate network formation to reduce polymerization shrinkage stress," Polymer Chemistry, vol. 8, No. 30, pp. 4301-4442, Aug. 14, 2017.

* cited by examiner

*Primary Examiner* — Jessica Whiteley
(74) *Attorney, Agent, or Firm* — Ann M. Knab; Thad McMurray

(57) ABSTRACT

Radically polymerizable composition which contains at least one vinyl ether according to general formula I:

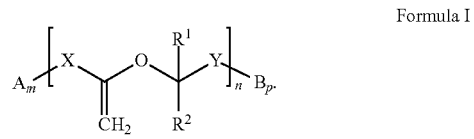

Formula I

19 Claims, No Drawings

POLYMER MATERIALS WITH UNSATURATED TRANSFER REAGENTS

CROSS-REFERENCE TO RELATED APPLICATIONS

This application claims priority to European patent application No. 18194789.6 filed on Sep. 17, 2018, the disclosure of which is incorporated herein by reference in its entirety.

TECHNICAL FIELD

The present invention relates to unsaturated transfer reagents and radically polymerizable compositions, which are suitable as materials for technical and medical applications, for example in surgery or ophthalmology and particularly as dental materials, e.g. as prosthesis materials, cements, filling composites, veneering materials or as materials for artificial teeth, inlays, onlays, crowns and bridges.

BACKGROUND

Radical polymers are formed by radical polymerization of one (homopolymers) or more (copolymers) radically polymerizable monomers. Depending on the functionality of the monomers being polymerized, linear polymers (in the case of monofunctional monomers) or crosslinked polymers (in the case of di- or multifunctional monomers) are obtained. On the one hand, radical polymerization has the advantage that many technically relevant monomers, such as e.g. ethylene, styrene, vinyl chloride, acrylonitrile, vinyl acetate, but also dienes, (meth)acrylates and (meth)acrylamides can be polymerized in this way. On the other hand, radical polymerization can be carried out in many different ways, e.g. in bulk (bulk polymerization), solution, suspension or emulsion. To trigger polymerization, radical-forming initiators are added, which form radicals through thermolysis, photolysis or redox reaction.

The radical polymerization proceeds according to a chain growth mechanism in which the polymerization-triggering primary radicals formed from the initiator add onto the double bond of the monomers. The thus-formed initiator radicals add many further monomer molecules in a rapid growth reaction until the growth of the polymer radicals is terminated by combination or disproportionation and the finished macromolecules are thus formed. Through the addition of chain transfer agents, so-called transfer reagents or regulators, the number-average molar mass of the formed polymer can be regulated in a targeted manner (cf. H. G. Elias, Makromoleküle, Vol. 1, 6th edition, Wiley-VCH, Weinheim etc. 199, 299-352).

Known chain transfer agents include, for example, mercaptans which, through the transfer of a hydrogen atom, form thiyl radicals which then in turn initiate the formation of a new polymer chain. Furthermore, double bond-containing reagents which react according to a radical addition-fragmentation chain transfer (AFCT) mechanism have proved to be particularly successful as chain transfer agents. Sulphur compounds, such as allyl sulphides, allyl sulphones, vinyl sulphone esters, dithioesters, dithiocarbamates, xanthates and trithiocarbonates are particularly effective as AFCT reagents and have been well studied (Moad et al., Polymer 49, 1079-1131 (2008)).

U.S. Pat. No. 2,694,699, which is hereby incorporated by reference, describes the homo- and copolymerization of α-sulphonyloxy acrylates. Alkyl mercaptans can be added as chain regulators.

U.S. Pat. No. 5,932,675, which is hereby incorporated by reference, discloses a process for the preparation of polymers with low molecular weight by radical polymerization, wherein the molecular weight is controlled through the addition e.g. of α-(t-butylthiomethyl)styrene as chain transfer reagent.

EP 3 090 722 A1 and corresponding US 2018369075, which is hereby incorporated by reference, describes radically polymerizable dental materials to which sulphonic acid esters are added as chain transfer reagent.

A disadvantage of sulphur-containing transfer reagents is that they can result in discoloration of the polymers and/or have a relatively high cellular toxicity.

U.S. Pat. No. 9,320,685 B2, which is hereby incorporated by reference, describes sulphur-free, unsaturated transfer reagents, such as e.g. compounds (2) or (3), which do not result in discoloration and are intended to reduce the shrinkage stress of dental composites.

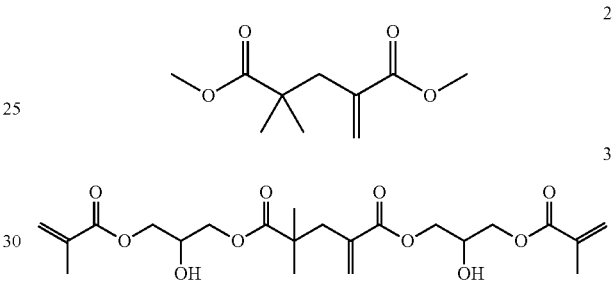

However, these transfer reagents have the disadvantage of a lower double-bond conversion and a reduced rate of polymerization (cf. P. K. Shah, J. W. Stansbury, C. N. Bowman, Polym. Chem. 2017; DOI:10.1039/c7py0072g).

SUMMARY

The object of the invention is to provide dental materials which, compared with known materials based on multifunctional (meth)acrylates, are characterized after curing by a narrower glass transition range, an improved impact resistance and a reduced polymerization shrinkage force accompanied by similar mechanical properties. Above all, the materials are intended to have a high reactivity and curing rate, no inherent colour and no unpleasant odour.

DETAILED DESCRIPTION

This object is achieved according to the invention by radically polymerizable compositions which contain at least one vinyl ether according to general formula I:

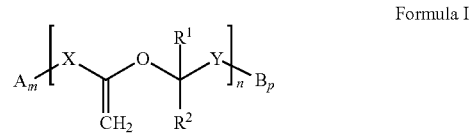

Formula I in which the variables have the following meanings:
A H, CN, a cycloaliphatic, linear or branched aliphatic $C_1$-$C_{30}$ hydrocarbon residue, which can be substituted by one or more, preferably 1 to 6, particularly preferably 1 to 3 substituents, preferably —$CH_3$, —$C_2H_5$, —OH, —OCH$_3$ and/or —O—COCH$_3$, which can be interrupted by one or more, preferably 1 to 4, particularly preferably 1 to 2 urethane groups, ester groups, O and/or S and which can contain 1 to 4, preferably 1 or 2 benzene groups, an aromatic C$_6$-C$_{30}$ hydrocarbon residue, which can be substituted by one or more, preferably 1 to 6, particularly preferably 1 to 3 substituents, preferably —CH$_3$, —C$_2$H$_5$, —OH, —OCH$_3$ and/or —O—COCH$_3$, or a combination thereof, wherein the hydrocarbon residues can bear a polymerizable group terminally;

X —COO—, —CON(R$^3$)— or is dispensed with, wherein the bonding to A is effected via O or N and wherein X is preferably dispensed with when A is an aromatic hydrocarbon residue or CN;

B H, CN, a cycloaliphatic, linear or branched aliphatic C$_1$-C$_{30}$ hydrocarbon residue, which can be substituted by one or more, preferably 1 to 6, particularly preferably 1 to 3 substituents, preferably —CH$_3$, —C$_2$H$_5$, —OH, —OCH$_3$ and/or —O—COCH$_3$, which can be interrupted by one or more, preferably 1 to 4, particularly preferably 1 to 2 urethane groups, ester groups, O and/or S and which can contain 1 to 4, preferably 1 or 2 benzene groups, an aromatic C$_6$-C$_{30}$ hydrocarbon residue, which can be substituted by one or more, preferably 1 to 6, particularly preferably 1 to 3 substituents, preferably —CH$_3$, —C$_2$H$_5$, —OH, —OCH$_3$ and/or —O—COCH$_3$, or a combination thereof, wherein the hydrocarbon residues can bear a polymerizable group terminally;

Y —COO—, —CON(R$^3$)— or is dispensed with, wherein the bonding to B is effected via O or N and wherein Y is preferably dispensed with when B is an aromatic hydrocarbon residue or CN;

R$^{1-3}$ in each case independently of one another hydrogen, a cycloaliphatic, linear or branched aliphatic C$_1$-C$_{10}$ hydrocarbon residue, which can be interrupted by one or more, preferably 1 to 4, particularly preferably 1 to 2 oxygen atoms and which can be substituted by one or more, preferably 1 to 4, particularly preferably 1 to 2 OH groups, or an aromatic C$_6$-C$_{10}$ hydrocarbon residue, which can be substituted by one or more, preferably 1 to 4, particularly preferably 1 to 2 OH groups;

m an integer from 1 to 6;
n an integer from 1 to 6;
p an integer from 1 to 6; wherein
m and p cannot be greater than 1 at the same time and wherein, if m=1, p=n, and if p=1, m=n.

The formula extends only to those compounds which are compatible with the theory of chemical valence. For example, if A is a C$_1$ residue, n can at most be 4. The indication that a residue is interrupted by one or more urethane groups, O atoms, S atoms etc. is to be understood such that these groups are in each case inserted into the carbon chain of the residue. These groups are thus bordered on both sides by C atoms and cannot be terminal. C$_1$ residues cannot be interrupted. The indication that a residue contains a benzene group means, in contrast, that this group can also be terminal, wherein any remaining yl-positions are saturated by H. By combinations is meant groups which are composed of the meanings given in each case, for example of aromatic and aliphatic residues, such as e.g. -Ph-CH$_2$-Ph-, or of several aromatic residues, such as e.g. -Ph-Ph-, or of aromatic and/or aliphatic residues and others of the named groups, such as e.g. -Ph-O-Ph- (Ph=phenyl).

The compounds of Formula 1 are active in radical polymerization as chain transfer agents and the use thereof as transfer reagent is likewise a subject of the invention.

Formula I is to be understood to mean that n of the group in brackets are bonded to the residue A or to the residue B. In the first case, m is equal to 1 and p is equal to n. In this case, Formula I can be simplified to Formula II:

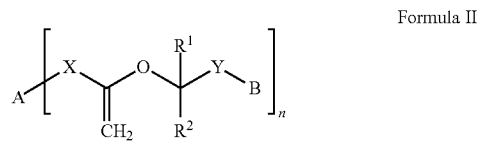

Formula II

In Formula II, 1 to 6 of the group in brackets are bonded to A in each case. In this case, A is an n-valent residue and B is a monovalent residue. In the case of Formula II, the variables preferably have the following meanings:

A H, CN, a cycloaliphatic, linear or branched aliphatic C$_1$-C$_{30}$ hydrocarbon residue, which can be substituted by one or more, preferably 1 to 6, particularly preferably 1 to 3 substituents, preferably —CH$_3$, —C$_2$H$_5$, —OH, —OCH$_3$ and/or —O—COCH$_3$, which can be interrupted by one or more, preferably 1 to 4, particularly preferably 1 to 2 urethane groups, ester groups, O and/or S and which can contain 1 to 4, preferably 1 or 2 benzene groups, an aromatic C$_6$-C$_{30}$ hydrocarbon residue, which can be substituted by one or more, preferably 1 to 6, particularly preferably 1 to 3 substituents, preferably —CH$_3$, —C$_2$H$_5$, —OH, —OCH$_3$ and/or —O—COCH$_3$, or a combination thereof, wherein the hydrocarbon residues can bear a polymerizable group terminally;

X —COO—, —CON(R$^3$)— or is dispensed with, wherein the bonding to A is effected via O or N and wherein X is preferably dispensed with when A is an aromatic hydrocarbon residue or CN;

B H, CN, a cycloaliphatic, linear or branched aliphatic C$_1$-C$_{30}$ hydrocarbon residue, which can be substituted by one or more, preferably 1 to 6, particularly preferably 1 to 3 substituents, preferably —CH$_3$, —C$_2$H$_5$, —OH, —OCH$_3$ and/or —O—COCH$_3$, which can be interrupted by one or more, preferably 1 to 4, particularly preferably 1 to 2 urethane groups, ester groups, O and/or S and which can contain 1 to 4, preferably 1 or 2 benzene groups, an aromatic C$_6$-C$_{30}$ hydrocarbon residue, which can be substituted by one or more, preferably 1 to 6, particularly preferably 1 to 3 substituents, preferably —CH$_3$, —C$_2$H$_5$, —OH, —OCH$_3$ and/or —O—COCH$_3$, or a combination thereof, wherein the hydrocarbon residues can bear a polymerizable group terminally;

Y —COO—, —CON(R$^3$)— or is dispensed with, wherein the bonding to B is effected via O or N and wherein Y is preferably dispensed with when B is an aromatic hydrocarbon residue or CN;

R$^{1-3}$ in each case independently of one another hydrogen, a cycloaliphatic, linear or branched aliphatic C$_1$-C$_{10}$ hydrocarbon residue, which can be interrupted by one or more, preferably 1 to 4, particularly preferably 1 to 2 oxygen atoms and which can be substituted by one or more, preferably 1 to 4, particularly preferably 1 to 2 OH groups, or an aromatic C$_6$-C$_{10}$ hydrocarbon residue, which can be substituted by one or more, preferably 1 to 4, particularly preferably 1 to 2 OH groups;

n an integer from 1 to 6.

Compounds of Formula II in which the variables have the following meanings are particularly preferred:

A cycloaliphatic, linear or branched aliphatic $C_1$-$C_{12}$ hydrocarbon residue, which can be substituted by 1 to 6, particularly preferably 1 to 3 substituents, preferably —$CH_3$, —$C_2H_5$, —OH and/or —$OCH_3$, which can be interrupted by 1 to 2 urethane groups, ester groups, O and/or S and which can contain 1 to 2 benzene groups, preferably 1,4-phenylene groups,
  an aromatic $C_6$-$C_{14}$ hydrocarbon residue, which can be substituted by 1 to 6, preferably 1 to 3 substituents, preferably —$CH_3$, —$C_2H_5$, —OH, —$OCH_3$ and/or —O—$COCH_3$,
  or a combination thereof, wherein the hydrocarbon residues can bear a polymerizable group, preferably a (meth)acrylate group, terminally;
X —COO—, —CON($R^3$)— or is dispensed with, wherein the bonding to A is effected via O or N and wherein X is preferably dispensed with when A is an aromatic hydrocarbon residue;
B cycloaliphatic, linear or branched aliphatic $C_1$-$C_{12}$ hydrocarbon residue, which can be interrupted by 1 to 2 urethane groups, ester groups, O and/or S and which can contain 1 to 2 benzene groups, preferably 1,4-phenylene groups,
  an aromatic $C_6$-$C_{14}$ hydrocarbon residue, which can be substituted by 1 to 6, preferably 1 to 3 substituents, preferably —$CH_3$, —$C_2H_5$, —OH, —$OCH_3$ and/or —O—$COCH_3$,
  or a combination thereof, wherein the hydrocarbon residues can bear a polymerizable group, preferably a (meth)acrylate group, terminally;
Y —COO—, —CON($R^3$)— or is dispensed with, wherein the bonding to B is effected via O or N and wherein Y is preferably dispensed with when B is an aromatic hydrocarbon residue;
$R^{1-3}$ in each case independently of one another hydrogen, a cycloaliphatic, linear or branched aliphatic $C_1$-$C_6$ hydrocarbon residue, which can be interrupted by 1 to 2 oxygen atoms and which can be substituted by 1 to 4, particularly preferably 1 to 2 OH groups, or
  an aromatic $C_6$-$C_{10}$ hydrocarbon residue, which can be substituted by 1 to 4, particularly preferably 1 to 2 OH groups;
n an integer from 1 to 3.

Compounds of Formula II in which the variables have the following meanings are quite particularly preferred:

A cycloaliphatic, linear or branched aliphatic $C_1$-$C_8$ hydrocarbon residue, which can be substituted by 1 to 3 substituents, preferably —$CH_3$, —$C_2H_5$, —OH and/or —$OCH_3$, which can be interrupted by 1 to 2 urethane groups, ester groups, O and/or S,
  an aromatic $C_6$-$C_{10}$ hydrocarbon residue, which can be substituted by 1 to 3 substituents, preferably —$CH_3$, —$C_2H_5$, —OH, —$OCH_3$ and/or —O—$COCH_3$,
  or a combination thereof, wherein the hydrocarbon residues can bear a polymerizable group, preferably a (meth)acrylate group, terminally;
X —COO—, —CON($R^3$)— or is dispensed with, wherein the bonding to A is effected via O or N and wherein X is preferably dispensed with when A is an aromatic hydrocarbon residue;
B cycloaliphatic, linear or branched aliphatic $C_1$-$C_8$ hydrocarbon residue, which can be interrupted by 1 to 2 urethane groups, ester groups, O and/or S,
  an aromatic $C_6$-$C_{10}$ hydrocarbon residue, which can be substituted by 1 to 3 substituents, preferably —$CH_3$, —$C_2H_5$, —OH, —$OCH_3$ and/or —O—$COCH_3$,
  or a combination thereof, wherein the hydrocarbon residues can bear a polymerizable group, preferably a (meth)acrylate group, terminally;
Y —COO— or is dispensed with, wherein the bonding to B is effected via O and wherein Y is preferably dispensed with when B is an aromatic hydrocarbon residue;
$R^{1-3}$ in each case independently of one another hydrogen, a cycloaliphatic, linear or branched aliphatic $C_1$-$C_4$ hydrocarbon residue, which can be interrupted by 1 to 2 oxygen atoms and which can be substituted by 1 to 2 OH groups, or
  an aromatic $C_6$ hydrocarbon residue, which can be substituted by 1 to 2 OH groups;
n 1 or 2.

In particular, those compounds of Formula II are preferred in which the variables have the following meanings:

A cycloaliphatic, linear or branched aliphatic $C_1$-$C_6$ hydrocarbon residue, which can be substituted by —$CH_3$, —$C_2H_5$, —OH or —$OCH_3$, which can be interrupted by 1 to 2 urethane groups, ester groups, O and/or S,
  an aromatic $C_6$ hydrocarbon residue, which can be substituted by 1 to 3 substituents, preferably —$CH_3$, —$C_2H_5$, —OH, —$OCH_3$ and/or —O—$COCH_3$,
  or a combination thereof, wherein the hydrocarbon residues can bear a polymerizable group, preferably a (meth)acrylate group, terminally;
X —COO—, —CON($R^3$)— or is dispensed with, wherein the bonding to A is effected via O or N and wherein X is preferably dispensed with when A is an aromatic hydrocarbon residue;
B cycloaliphatic, linear or branched aliphatic $C_1$-$C_6$ hydrocarbon residue, which can be interrupted by 1 to 2 urethane groups, ester groups, O and/or S,
  an aromatic $C_6$ hydrocarbon residue, which can be substituted by 1 to 3 substituents, preferably —$CH_3$, —$C_2H_5$, —OH, —$OCH_3$ and/or —O—$COCH_3$,
  or a combination thereof, wherein the hydrocarbon residues can bear a polymerizable group, preferably a (meth)acrylate group, terminally;
Y —COO— or is dispensed with, wherein the bonding to B is effected via O and wherein Y is preferably dispensed with when B is an aromatic hydrocarbon residue;
$R^{1-3}$ in each case independently of one another hydrogen, a linear or branched aliphatic $C_1$-$C_2$ hydrocarbon residue, which can be interrupted by an oxygen atom and which can be substituted by an OH group, preferably —$CH_3$, —$CH_2$—$CH_3$ or —$OCH_3$;
n 1 or 2.

If several of the group in brackets are bonded to the residue B, p is equal to 1 and m is equal to n. In this case, Formula I can be simplified to Formula III:

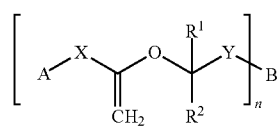

Formula III

In Formula III, 1 to 6 of the group in brackets are bonded to B in each case. In this case, A is a monovalent residue and B is an n-valent residue. In the case of Formula III, the variables preferably have the following meanings:

A H, CN, a cycloaliphatic, linear or branched aliphatic $C_1$-$C_{30}$ hydrocarbon residue, which can be substituted by one or more, preferably 1 to 6, particularly preferably 1 to 3 substituents, preferably —$CH_3$, —$C_2H_5$, —OH, —$OCH_3$ and/or —O—$COCH_3$, which can be interrupted by one or more, preferably 1 to 4, particularly preferably 1 to 2 urethane groups, ester groups, O and/or S and which can contain 1 to 4, preferably 1 or 2 benzene groups, an aromatic $C_6$-$C_{30}$ hydrocarbon residue, which can be substituted by one or more, preferably 1 to 6, particularly preferably 1 to 3 substituents, preferably —$CH_3$, —$C_2H_5$, —OH, —$OCH_3$ and/or —O—$COCH_3$,
or a combination thereof, wherein the hydrocarbon residues can bear a polymerizable group terminally;

X —COO—, —CON($R^3$)— or is dispensed with, wherein the bonding to A is effected via O or N and wherein X is preferably dispensed with when A is an aromatic hydrocarbon residue or CN;

B H, CN, a cycloaliphatic, linear or branched aliphatic $C_1$-$C_{30}$ hydrocarbon residue, which can be substituted by one or more, preferably 1 to 6, particularly preferably 1 to 3 substituents, preferably —$CH_3$, —$C_2H_5$, —OH, —$OCH_3$ and/or —O—$COCH_3$, which can be interrupted by one or more, preferably 1 to 4, particularly preferably 1 to 2 urethane groups, ester groups, O and/or S and which can contain 1 to 4, preferably 1 or 2 benzene groups, an aromatic $C_6$-$C_{30}$ hydrocarbon residue, which can be substituted by one or more, preferably 1 to 6, particularly preferably 1 to 3 substituents, preferably —$CH_3$, —$C_2H_5$, —OH, —$OCH_3$ and/or —O—$COCH_3$,
or a combination thereof, wherein the hydrocarbon residues can bear a polymerizable group terminally;

Y —COO—, —CON($R^3$)— or is dispensed with, wherein the bonding to B is effected via O or N and wherein Y is preferably dispensed with when B is an aromatic hydrocarbon residue or CN;

$R^{1-3}$ in each case independently of one another hydrogen, a cycloaliphatic, linear or branched aliphatic $C_1$-$C_{10}$ hydrocarbon residue, which can be interrupted by one or more, preferably 1 to 4, particularly preferably 1 to 2 oxygen atoms and which can be substituted by one or more, preferably 1 to 4, particularly preferably 1 to 2 OH groups, or
an aromatic $C_6$-$C_{10}$ hydrocarbon residue, which can be substituted by one or more, preferably 1 to 4, particularly preferably 1 to 2 OH groups;

n an integer from 1 to 6.

Compounds of Formula III in which the variables have the following meanings are particularly preferred:

A cycloaliphatic, linear or branched aliphatic $C_1$-$C_{12}$ hydrocarbon residue, which can be substituted by 1 to 6, particularly preferably 1 to 3 substituents, preferably —$CH_3$, —$C_2H_5$, —OH and/or —$OCH_3$, which can be interrupted by 1 to 2 urethane groups, ester groups, O and/or S and which can contain 1 to 2 benzene groups, preferably 1,4-phenylene groups,
an aromatic $C_6$-$C_{14}$ hydrocarbon residue, which can be substituted by 1 to 6, preferably 1 to 3 substituents, preferably —$CH_3$, —$C_2H_5$, —OH, —$OCH_3$ and/or —O—$COCH_3$,
or a combination thereof, wherein the hydrocarbon residues can bear a polymerizable group, preferably a (meth)acrylate group, terminally;

X —COO—, —CON($R^3$)— or is dispensed with, wherein the bonding to A is effected via O or N and wherein X is preferably dispensed with when A is an aromatic hydrocarbon residue;

B cycloaliphatic, linear or branched aliphatic $C_1$-$C_{12}$ hydrocarbon residue, which can be interrupted by 1 to 2 urethane groups, ester groups, O and/or S and which can contain 1 to 2 benzene groups, preferably 1,4-phenylene groups,
an aromatic $C_6$-$C_{14}$ hydrocarbon residue, which can be substituted by 1 to 6, preferably 1 to 3 substituents, preferably —$CH_3$, —$C_2H_5$, —OH, —$OCH_3$ and/or —O—$COCH_3$,
or a combination thereof, wherein the hydrocarbon residues can bear a polymerizable group, preferably a (meth)acrylate group, terminally;

Y —COO—, —CON($R^3$)— or is dispensed with, wherein the bonding to B is effected via O or N and wherein Y is preferably dispensed with when B is an aromatic hydrocarbon residue;

$R^{1-3}$ in each case independently of one another hydrogen, a cycloaliphatic, linear or branched aliphatic $C_1$-$C_6$ hydrocarbon residue, which can be interrupted by 1 to 2 oxygen atoms and which can be substituted by 1 to 4, particularly preferably 1 to 2 OH groups, or
an aromatic $C_6$-$C_{10}$ hydrocarbon residue, which can be substituted by 1 to 4, particularly preferably 1 to 2 OH groups;

n an integer from 1 to 3.

Compounds of Formula III in which the variables have the following meanings are quite particularly preferred:

A cycloaliphatic, linear or branched aliphatic $C_1$-$C_8$ hydrocarbon residue, which can be substituted by 1 to 3 substituents, preferably —$CH_3$, —$C_2H_5$, —OH and/or —$OCH_3$, which can be interrupted by 1 to 2 urethane groups, ester groups, O and/or S,
an aromatic $C_6$-$C_{10}$ hydrocarbon residue, which can be substituted by 1 to 3 substituents, preferably —$CH_3$, —$C_2H_5$, —OH, —$OCH_3$ and/or —O—$COCH_3$,
or a combination thereof, wherein the hydrocarbon residues can bear a polymerizable group, preferably a (meth)acrylate group, terminally;

X —COO—, —CON($R^3$)— or is dispensed with, wherein the bonding to A is effected via O or N and wherein X is preferably dispensed with when A is an aromatic hydrocarbon residue;

B cycloaliphatic, linear or branched aliphatic $C_1$-$C_8$ hydrocarbon residue, which can be interrupted by 1 to 2 urethane groups, ester groups, O and/or S,
an aromatic $C_6$-$C_{10}$ hydrocarbon residue, which can be substituted by 1 to 3 substituents, preferably —$CH_3$, —$C_2H_5$, —OH, —$OCH_3$ and/or —O—$COCH_3$,
or a combination thereof, wherein the hydrocarbon residues can bear a polymerizable group, preferably a (meth)acrylate group, terminally;

Y —COO— or is dispensed with, wherein the bonding to B is effected via O and wherein Y is preferably dispensed with when B is an aromatic hydrocarbon residue;

$R^{1-3}$ in each case independently of one another hydrogen, a cycloaliphatic, linear or branched aliphatic $C_1$-$C_4$ hydrocarbon residue, which can be interrupted by 1 to 2 oxygen atoms and which can be substituted by 1 to 2 OH groups, or
an aromatic $C_6$ hydrocarbon residue, which can be substituted by 1 to 2 OH groups;

n 1 or 2.

In particular, those compounds of Formula III are preferred in which the variables have the following meanings:

A cycloaliphatic, linear or branched aliphatic $C_1$-$C_6$ hydrocarbon residue, which can be substituted by —$CH_3$, —$C_2H_5$, —OH or —$OCH_3$, which can be interrupted by 1 to 2 urethane groups, ester groups, O and/or S, an aromatic $C_6$ hydrocarbon residue, which can be substituted by 1 to 3 substituents, preferably —$CH_3$, —$C_2H_5$, —OH, —$OCH_3$ and/or —O—$COCH_3$, or a combination thereof, wherein the hydrocarbon residues can bear a polymerizable group, preferably a (meth)acrylate group, terminally;

X —COO—, —$CON(R^3)$— or is dispensed with, wherein the bonding to A is effected via O or N and wherein X is preferably dispensed with when A is an aromatic hydrocarbon residue;

B cycloaliphatic, linear or branched aliphatic $C_1$-$C_6$ hydrocarbon residue, which can be interrupted by 1 to 2 urethane groups, ester groups, O and/or S, an aromatic $C_6$ hydrocarbon residue, which can be substituted by 1 to 3 substituents, preferably —$CH_3$, —$C_2H_5$, —OH, —$OCH_3$ and/or —O—$COCH_3$, or a combination thereof, wherein the hydrocarbon residues can bear a polymerizable group, preferably a (meth)acrylate group, terminally;

Y —COO— or is dispensed with, wherein the bonding to B is effected via O and wherein Y is preferably dispensed with when B is an aromatic hydrocarbon residue;

$R^{1-3}$ in each case independently of one another hydrogen, a linear or branched aliphatic $C_1$-$C_2$ hydrocarbon residue, which can be interrupted by an oxygen atom and which can be substituted by an OH group, preferably —$CH_3$, —$CH_2$—$CH_3$ or —$OCH_3$;

n 1 or 2.

For the sake of simplicity, the names of monovalent residues, such as phenyl and naphthyl, are also used herein for polyvalent residues with more than one yl-position, wherein the respective meaning follows from Formulae 1, 2 and 3. Phenyl (Ph) thus includes phenylene and benzene-1,3,5-triyl in particular. Naphthyl preferably represents a naphthalene-2,6-diyl residue.

Compounds of Formula I according to the invention can be prepared in the style of similar known compounds but are themselves not known from the literature. Here, in the first step, a tertiary alcohol is linked to a halide under basic conditions. In the second step, a strong, non-nucleophilic base is used for deprotonation and hydroxymethylation. The hydroxymethylation can be carried out on the central methylene group following Deguest et al. (G. Deguest, L. Bischoff, C. Fruit, F. Marsais, *Org. Lett.* 2007, 9, 1165-1167) and Rehbein et al. (J. Rehbein, S. Leick, M. Hiersemann, *Journal of Organic Chemistry* 2009, 74 (4), 1531-1540), wherein benzotriazole-1-methanol is used as the reagent. The last step also takes place under basic conditions, wherein mesylation is effected first and then elimination. In the preliminary or intermediate stages, the protective group technique can optionally be used:

Step 1:

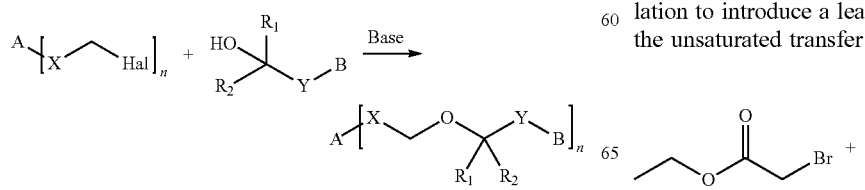

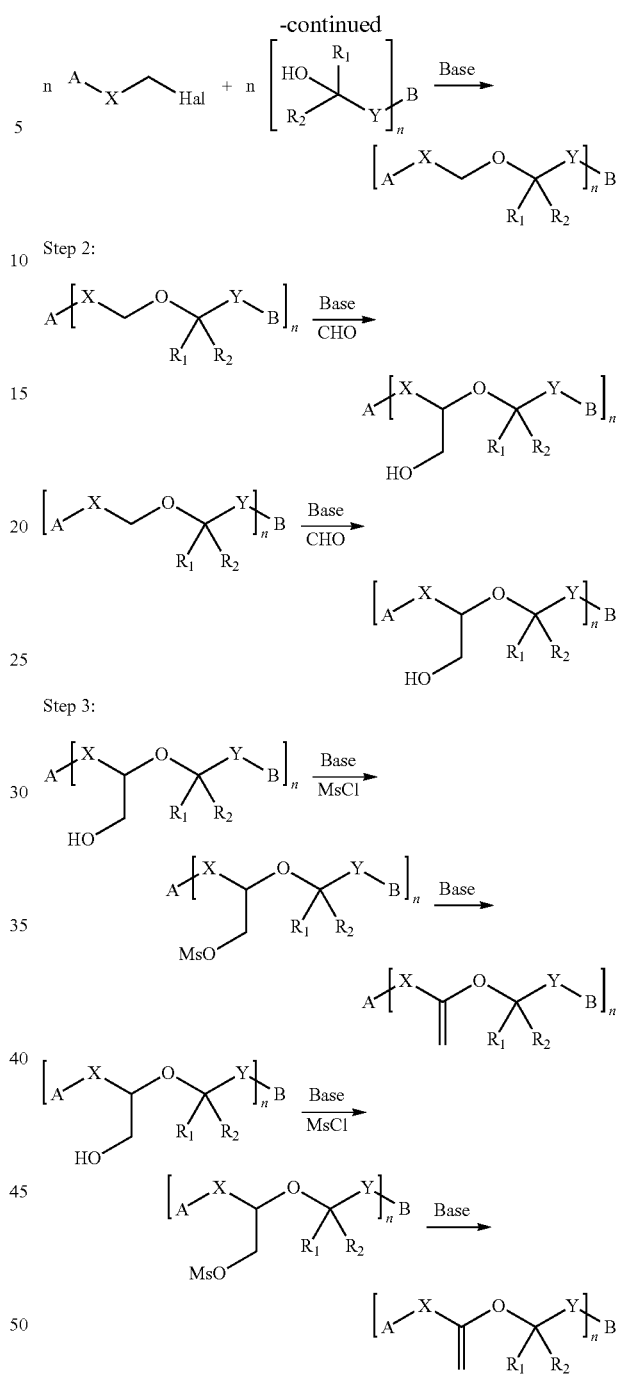

The particularly preferred 2-((1-ethoxy-2-methyl-1-oxopropan-2-yl)oxy)acrylic acid ethyl ester (1) can preferably be prepared by first of all reacting ethyl bromoacetate with ethyl 2-hydroxyisobutyrate and then hydroxymethylating the product with benzotriazole-1-methanol. After the mesylation to introduce a leaving group, the elimination to form the unsaturated transfer reagent (1) is effected with DBU.

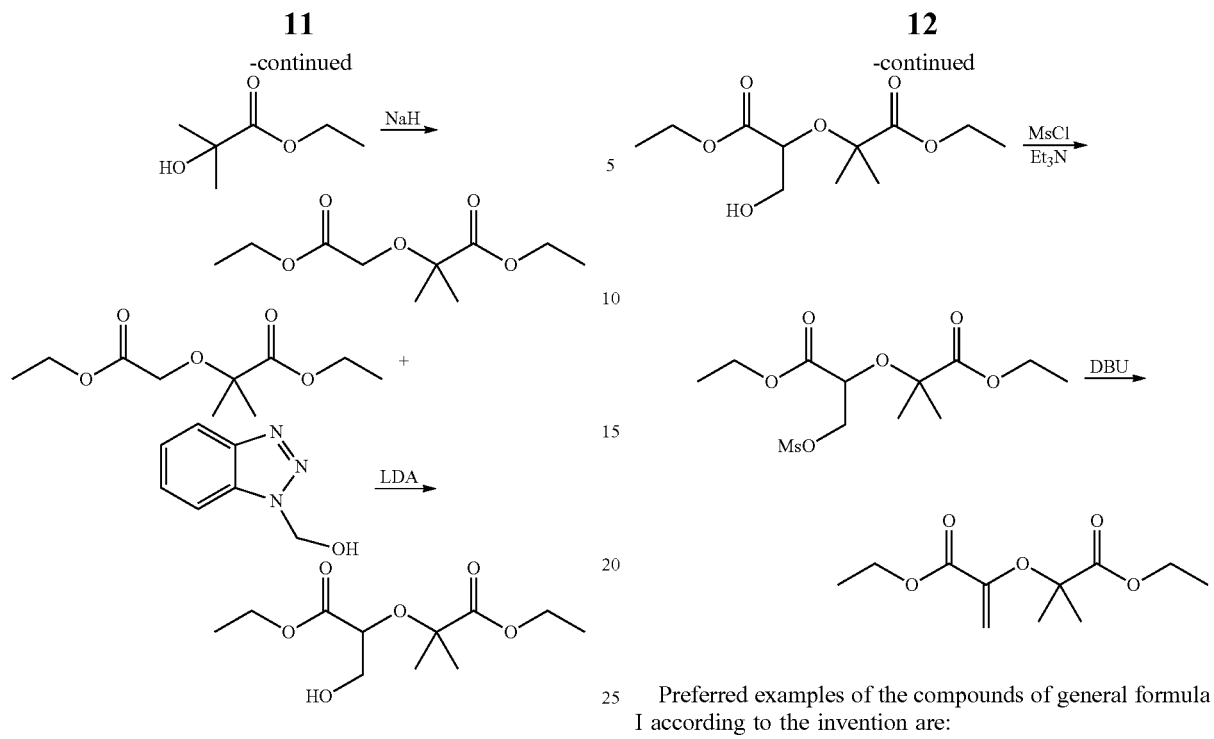
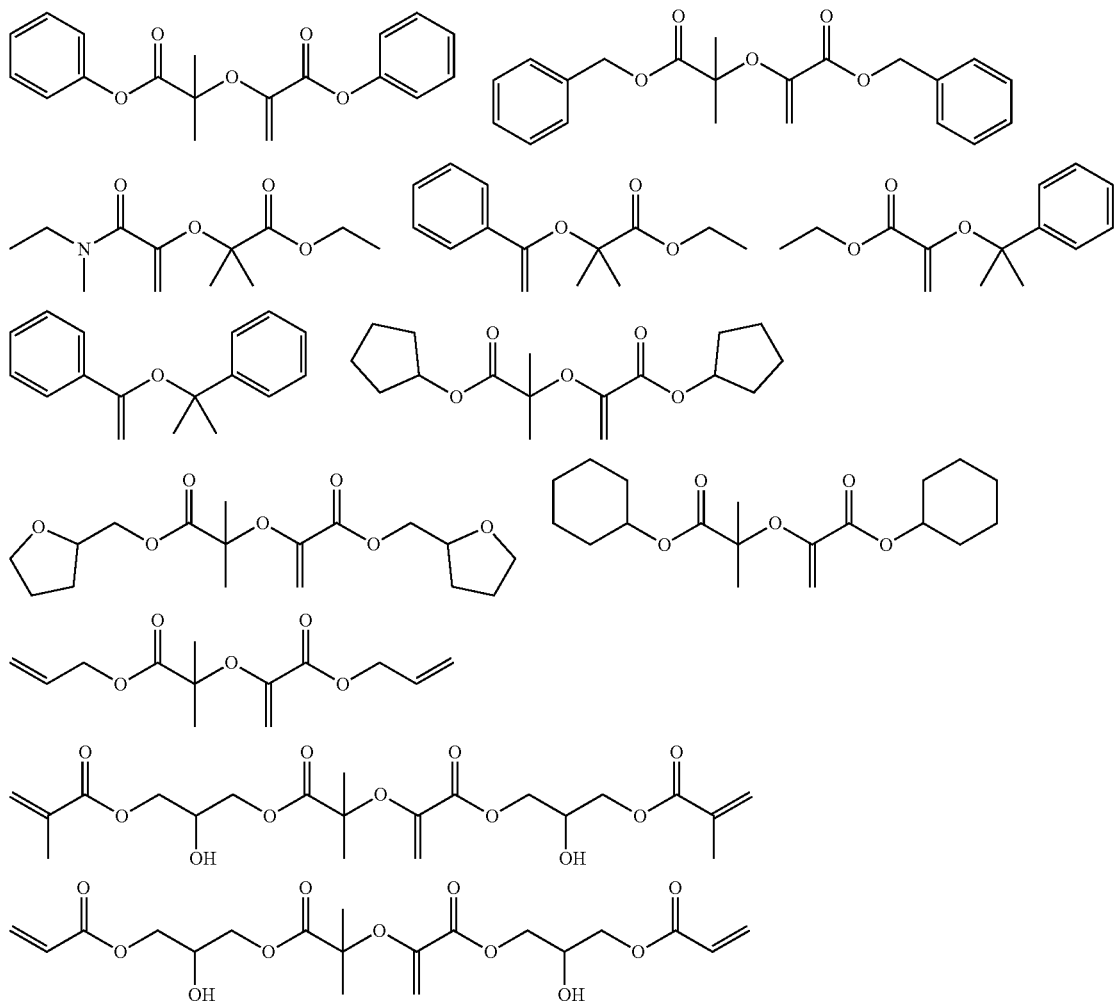
Preferred examples of the compounds of general formula I according to the invention are:

-continued
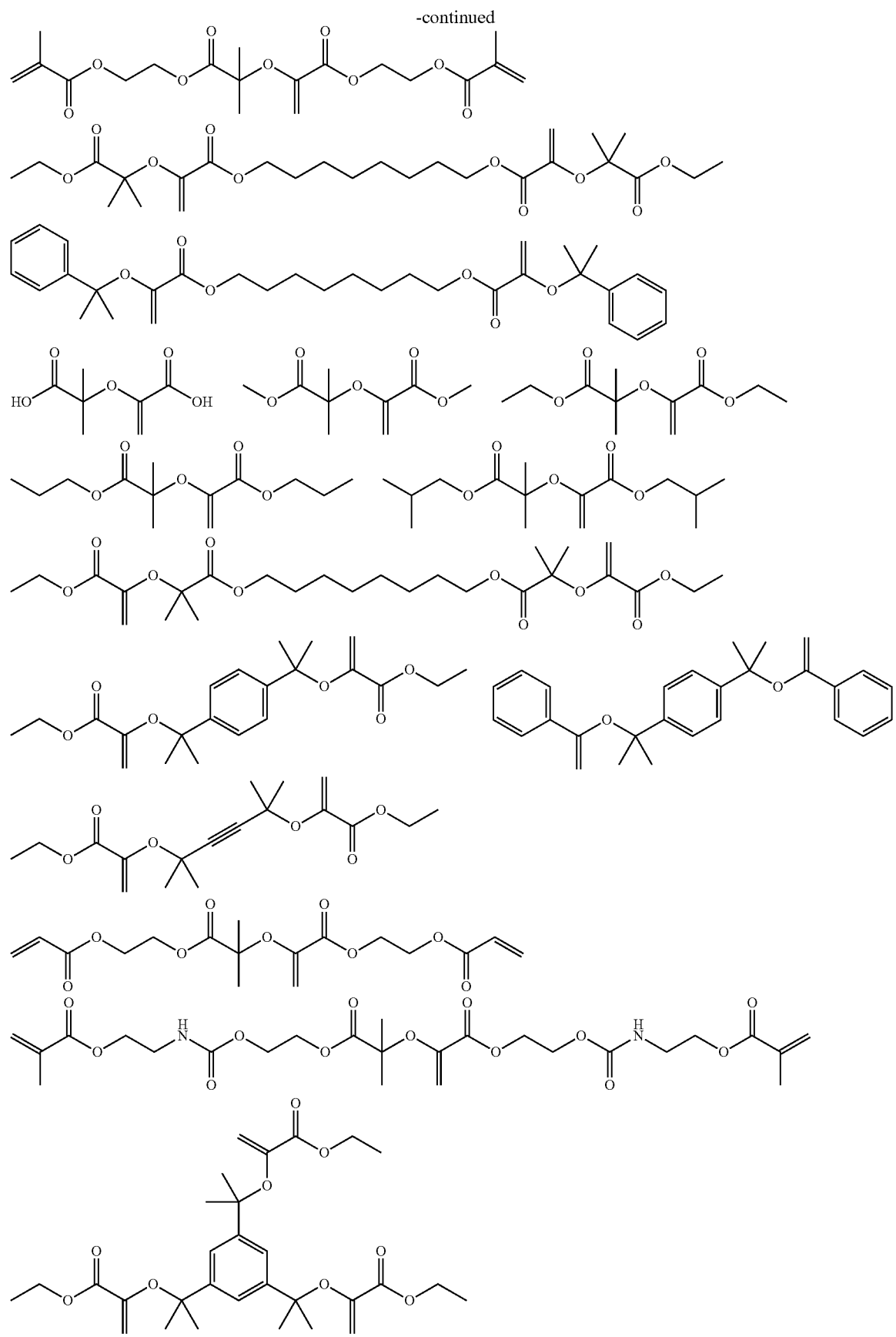

Particularly preferred compounds according to the invention according to general formula I where n=1 are:

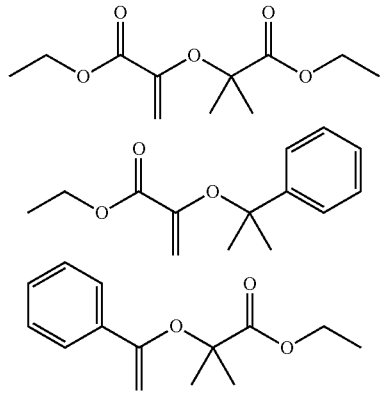

Particularly preferred compounds according to the invention according to Formula II where n=2 are:

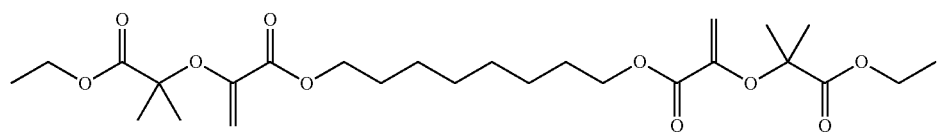

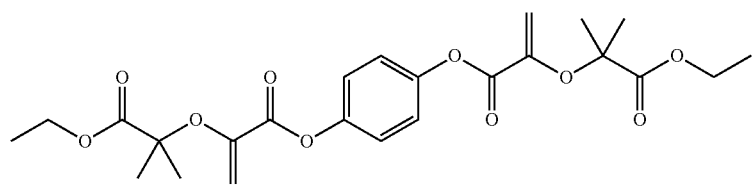

Particularly preferred compounds according to the invention according to Formula III where n=2 are:

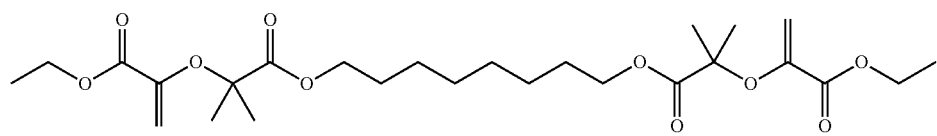

Furthermore, a particularly preferred compound according to the invention according to Formula III where n=3 is:

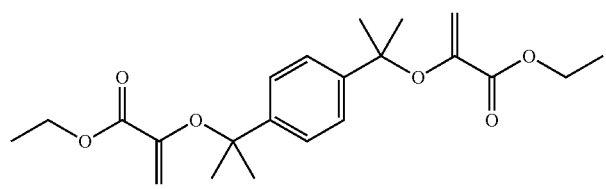

The compounds of Formula I according to the invention can advantageously be used as chain transfer agents to control and regulate the network structure during the polymerization of mono(meth)acrylates, multifunctional (meth) acrylates and mixtures thereof. Herein, chain transfer agents are also referred to as transfer reagents or regulators. In comparison with pure (meth)acrylates, they result in polymer networks with a narrower glass transition, that is the glass transition takes place in a narrower temperature range, and a considerably reduced glass transition temperature. A reduced glass transition temperature has the advantage that the polymers can be softened at lower temperatures. This allows the adhesive bond to be released in a targeted manner (debonding-on-demand), e.g. in the case of adhesives and cements. In addition, more homogeneous polymer networks are obtained, i.e. networks which are characterized in that they have a narrower distribution of the molar mass between the crosslinking points. This has the advantage that chain stresses can be better relieved by relaxation processes and that a more rapid debonding-on-demand (DoD) can be achieved, e.g. in the field of dental cements. It is particularly advantageous that, in the case of the polymerization of (meth)acrylates, the compounds of Formula I reduce the glass transition temperature of the materials being polymerized without appreciably reducing the rate of polymerization.

Furthermore, the materials obtained are characterized by an improved impact resistance, which is highly advantageous e.g. in the case of stereolithographically produced shaped bodies or in the case of dental prostheses.

In the case of the crosslinking polymerization of e.g. multifunctional (meth)acrylates, the compounds of Formula I additionally bring about a considerably delayed gel formation and thus guarantee a longer gel time without negatively impacting on the conversion, i.e. that the three-dimensional polymer network only forms later. The extended gel time has an advantageous effect on the polymerization shrinkage stress because internal stresses can thereby be compensated for over a longer period by flow processes. This results in considerably lower shrinkage stresses, which is highly advantageous e.g. in the case of shaped parts with complex geometries or dental filling composites.

The compounds of Formula I can therefore be used to reduce the glass transition temperature, to reduce the polymerization shrinkage force and/or to improve the impact resistance of polymers. The polymerization shrinkage force is also referred to as polymerization shrinkage stress.

The materials according to the invention are additionally characterized by an advantageous storage modulus at room temperature $G'_{(25°\,C.)}$ and an improved elongation at break, with the result that the materials have mechanical properties that are advantageous in the case of stereolithographically produced shaped bodies or in the case of dental prostheses. The storage modulus G' is proportional to the proportion of deformation energy that is stored in the material and can be recovered from the material after load removal. The elongation at break is the elongation value last recorded before the stress drops to less than or equal to 10% of the strength value. As a value it is usually quoted as a percentage (%).

According to the invention, those materials are preferred which, in addition to a compound of Formula I, additionally contain at least one radically polymerizable monomer and preferably also at least one initiator for the radical polymerization.

Materials which contain at least one multifunctional (meth)acrylate or a mixture of mono- and multifunctional (meth)acrylates as radically polymerizable monomer are particularly preferred. By monofunctional (meth)acrylates is meant compounds with one, by polyfunctional (meth)acrylates is meant compounds with two or more, preferably 2 to 4, radically polymerizable groups. According to a quite particularly preferred embodiment, the compositions according to the invention contain at least one dimethacrylate or a mixture of mono- and dimethacrylates. Materials which contain mono- and multifunctional (meth)acrylates as radically polymerizable monomer are particularly suitable as dental materials, wherein methacrylates are preferred for materials which are cured intraorally.

Examples of particularly suitable mono- or multifunctional (meth)acrylates are methyl, ethyl, 2-hydroxyethyl, butyl, benzyl, tetrahydrofurfuryl or isobornyl (meth)acrylate, p-cumylphenoxyethylene glycol methacrylate (CMP-1E), 2-(2-biphenyloxy)-ethyl methacrylate, bisphenol A di(meth)acrylate, bis-G(M)A (an addition product of (meth)acrylic acid and bisphenol A diglycidyl ether), ethoxylated or propoxylated bisphenol A di(meth)acrylate, such as e.g. 2-[4-(2-(meth)acryloyloxyethoxyethoxy)phenyl]-2-[4-(2-methacryloyloxyethoxy)phenyl]-propane) (SR-348c, Sartomer; contains 3 ethoxy groups) or 2,2-bis[4-(2-(meth)acryloxypropoxy)phenyl]propane, 1,6-bis-[2-(meth)acryloyloxyethoxycarbonylamino]-2,2,4-trimethylhexane (UD(M)A; (an addition product of 2-hydroxyethyl (meth)acrylate and 2,2,4-trimethylhexamethylene diisocyanate), di-, tri- or tetraethylene glycol di(meth)acrylate, trimethylolpropane tri(meth)acrylate, pentaerythritol tetra(meth)acrylate, as well as glycerol di- and tri(meth)acrylate, 1,4-butanediol di(meth)acrylate, 1,10-decanediol di(meth)acrylate ($D_3MA$) or 1,12-dodecanediol di(meth)acrylate. Quite particularly suitable mono- or multifunctional (meth)acrylates are methyl, butyl, tetrahydrofurfuryl or isobornyl (meth)acrylate, p-cumylphenoxyethylene glycol methacrylate (CMP-1E), bisphenol A di(meth)acrylate, SR-348c, UD(M)A; tri- or tetraethylene glycol di(meth)acrylate, glycerol tri(meth)acrylate, 1,10-decanediol di(meth)acrylate ($D_3MA$) or 1,12-dodecanediol di(meth)acrylate.

In addition, thermo- or photolabile di(meth)acrylates, such as e.g. the addition product of 2 mol 2-acetoacetoxyethyl methacrylate and 1 mol 2,2,4-trimethylhexamethylene-1,6-diisocyanate (thermolabile) or methacrylic acid 2-[2-(4-{2-methyl-2-[2-(methacryloyloxy)-ethylcarbamoyloxy]propionyl}phenoxy)-ethoxycarbonylamino]ethyl ester are also suitable. Mixtures of thermo- or photolabile monomers, such as e.g. the addition product of 2 mol 2-acetoacetoxyethyl methacrylate and 1 mol 2,2,4-trimethylhexamethylene-1,6-diisocyanate (thermolabile), and compounds of Formulae I and II are particularly suitable for materials with debonding-on-demand properties.

The materials according to the invention furthermore preferably contain at least one photoinitiator or thermal initiator for the radical polymerization, particularly preferably a photoinitiator, in particular a photoinitiator which is active in a wavelength range of from 400 to 500 nm.

Preferred photoinitiators are benzophenone, benzoin, α-diketones, such as 9,10-phenanthrenequinone, 1-phenylpropane-1,2-dione, diacetyl or 4,4'-dichlorobenzil or derivatives thereof, particularly preferably camphorquinone (CQ) and 2,2-dimethoxy-2-phenylacetophenone, and mixtures thereof.

The photoinitiators are preferably used in combination with accelerators. Tertiary amines, such as e.g. tertiary aromatic amines, in particular N,N-dialkyl-anilines, -p-toluidines or -3,5-xylidines, p-N,N-dialkylamino-phenylethanol, -benzoic acid derivatives, -benzaldehyde, -phenylacetic acid ester and -phenylpropionic acid ester, are particularly suitable as accelerators. α-diketones in combination with amines as reducing agent, such as e.g. 4-(dimethylamino)-benzoic acid ethyl ester (EDMAB), N,N-dimethylaminoethyl methacrylate, N,N-dimethyl-sym.-xylidine or triethanolamine, are quite particularly preferred.

Additionally preferred photoinitiators are Norrish type I photoinitiators, preferably acyl- or bisacylphosphine oxides, and particularly preferably monoacyltrialkyl-, diacyldialkylgermanium and tetraacylgermanium compounds as well as tetraacylstannanes, such as e.g. benzoyltrimethylgermanium, dibenzoyldiethylgermanium, bis(4-methoxybenzoyl)

diethylgermanium (MBDEGe, Ivocerin®), tetrabenzoylgermanium, tetrakis(2-methylbenzoyl)germanium, tetrakis(o-methylbenzoyl)germanium or tetrakis(mesitoyl)stannane. Acyl- and bisacylgermanium compounds have the advantage that they decolour after the irradiation (bleaching effect) and thus do not impair the transparency of the cured materials. In addition, they are monomolecular photoinitiators, i.e. they do not require an accelerator in order to reach their full activity.

Mixtures of the various above-named photoinitiators, such as e.g. a mixture of bis(4-methoxybenzoyl)diethylgermanium or tetrakis(o-methylbenzoyl)germanium with camphorquinone and 4-dimethylaminobenzoic acid ethyl ester, are furthermore preferred.

The materials according to the invention can contain one or more further initiators for the radical polymerization, in particular thermal initiators which are suitable for heat curing, preferably azo compounds, such as e.g. 2,2'-azobis (isobutyronitrile) (AIBN) or azobis-(4-cyanovaleric acid), peroxides, such as e.g. dibenzoyl peroxide, dilauroyl peroxide, tert-butyl peroctoate, Cert-butyl perbenzoate or di-(tert-butyl) peroxide, or redox initiator combinations, such as e.g. combinations of benzoyl peroxide with amines, such as e.g. N,N-dimethyl-p-toluidine, N,N-dihydroxyethyl-p-toluidine, p-dimethylaminobenzoic acid ethyl ester or N,N-dimethyl-sym.-xylidine, combinations of inorganic peroxides, such as e.g. potassium and ammonium peroxodisulphate, with reducing agents, such as e.g. sulphite, hydrogen sulphite, thiosulphate, sulphinic acids, amines, endiols or Fe(II) salts, redox systems consisting of organic peroxides or hydroperoxides and reducing agents, such as e.g. ascorbic acid, barbiturates, thioureas or sulphinic acids.

Furthermore, compounds of transition metals which have at least two stable valency stages can be used as transition metal redox initiators. That is above all compounds of the elements copper, iron, vanadium, nickel or cobalt, wherein copper compounds are particularly preferred and these are preferably used as well-organosoluble compounds, such as e.g. as acetylacetonate, naphthenate or 2-ethylhexanoate.

According to a preferred embodiment, the materials according to the invention, in particular dental materials, additionally contain organic or preferably inorganic particulate filler, particularly preferably one or more inorganic particulate fillers. Mixtures which contain monomers, preferably multifunctional (meth)acrylates, mixtures thereof or mixtures of multifunctional and monofunctional (meth)acrylates, and fillers are referred to as composites.

Preferred inorganic particulate fillers are oxides, such as $SiO_2$, $ZrO_2$ and $TiO_2$ or mixed oxides of $SiO_2$, $ZrO_2$, $ZnO$ and/or $TiO_2$ with a particle size of from 0.010 to 15 µm, nanoparticulate or microfine fillers with a particle size of from 10 to 300 nm, such as pyrogenic silica or precipitated silica, as well as glass powder, such as quartz, glass ceramic or radiopaque glass powder, preferably barium- or strontium-aluminium silicate glasses, with a particle size of from 0.01 to 15 µm, preferably from 0.2 to 1.5 µm, and radiopaque fillers, such as ytterbium trifluoride, tantalum(V) oxide, barium sulphate or mixed oxides of $SiO_2$ with ytterbium(III) oxide or tantalum(V) oxide, with a particle size of from 0.2 to 5 µm. Furthermore, the dental materials according to the invention can contain fibrous fillers, nanofibres, whiskers or mixtures thereof. Particularly preferred fillers are $SiO_2$ and $ZrO_2$, mixed oxides of $SiO_2$ and $ZrO_2$, pyrogenic silica as well as glass powder of barium- or strontium-aluminium silicate glasses and ytterbium trifluoride. Quite particularly preferred fillers are $SiO_2$, mixed oxides of $SiO_2$ and $ZrO_2$, pyrogenic silica as well as glass powder of barium-aluminium silicate glasses and ytterbium trifluoride.

Unless otherwise indicated, all particle sizes are weight-average particle sizes, in which the particle size is determined by means of static light scattering, preferably using an LA-960 static laser scattering particle size analyzer (Horiba, Japan). Here, a laser diode with a wavelength of 655 nm and an LED with a wavelength of 405 nm are used as light sources in a measurement range of from 0.1 to 1000 µm. The use of two light sources with different wavelengths makes it possible to measure the entire particle size distribution of a sample in only one measurement pass, wherein the measurement is carried out as a wet measurement. For this a 0.1 to 0.5% aqueous dispersion of the filler is prepared and the scattered light thereof is measured in a flow-through cell. The scattered light analysis for the calculation of particle size and particle size distribution is effected according to the Mie theory in accordance with DIN/ISO 13320.

The measurement of the particle size below 100 nm is preferably effected by dynamic light scattering (DLS) of aqueous particle dispersions using an ALV/CGS-3 Compact Goniometer (ALV-Laser Vertriebsgesellschaft, Langen, Germany) with an He—Ne laser with a wavelength of 633 nm, at a scattering angle of 90° at 25° C.

The light scattering decreases as the particle size decreases, however fillers with a small particle size have a greater thickening action. The fillers are subdivided into macrofillers and microfillers according to the particle size. Macrofillers are obtained e.g. by grinding quartz, radiopaque glasses, borosilicates or ceramic, are purely inorganic in nature and usually consist of splintery parts. Macrofillers with an average particle size of from 0.2 to 15 µm are preferred. Pyrogenic $SiO_2$ or precipitated silica is preferably used as microfiller or else mixed oxides, e.g. $SiO_2$—$ZrO_2$, which are accessible by hydrolytic co-condensation of metal alkoxides. The microfillers preferably have an average particle size of from 5 to 100 nm.

The fillers are preferably surface-modified, particularly preferably by silanization, quite particularly preferably by radically polymerizable silanes, in particular with 3-methacryl-oyloxypropyltrimethoxysilane. For the surface modification of non-silicate fillers, e.g. of $ZrO_2$ or $TiO_2$, functionalized acidic phosphates, such as 10-methacryloyloxydecyl dihydrogen phosphate, can also be used.

The filling level depends on the desired intended application. Composite cements preferably have a filler content of from 5 to 70 wt.-% and filling composites have a filler content of from 70 to 85 wt.-%.

The compositions according to the invention can optionally contain further additives, above all stabilizers, colorants, antibacterial active ingredients, fluoride-ion-releasing additives, blowing agents, optical brighteners, plasticizers or UV absorbers.

The compositions based on the compounds according to the invention according to general formula I and mixtures thereof with mono- and/or multifunctional (meth)acrylates preferably contain the following components:

a) 0.1 to 30 wt.-%, preferably 1 to 25 wt.-% and particularly preferably 1 to 15 wt.-% of at least one compound according to general formula I, b) 0.01 to 5 wt.-%, particularly preferably 0.1 to 3.0 wt.-% of at least one initiator for the radical polymerization, c) 1 to 90 wt.-%, preferably 1 to 80 wt.-% and particularly preferably 10 to 80 wt.-% of at least one mono- or multifunctional (meth)acrylate, d) 0 to 85 wt.-%, preferably 0 to 80 wt.-% and particularly preferably 0 to 75 wt.-% of at least one filler.

Compositions without filler preferably contain the following components:

a) 0.1 to 30 wt.-%, preferably 1 to 25 wt.-% and particularly preferably 1 to 15 wt.-% of at least one compound according to general formula I,
b) 0.01 to 5 wt.-%, particularly preferably 0.1 to 3.0 wt.-% of at least one initiator for the radical polymerization,
c) 1 to 90 wt.-%, preferably 1 to 80 wt.-% and particularly preferably 10 to 80 wt.-% of at least one mono- or multifunctional (meth)acrylate.

Filler-free compositions are suitable in particular as prosthesis materials or for the production of shaped bodies by stereolithography or 3D printing.

Filler-containing compositions preferably contain the following components:

a) 0.1 to 30 wt.-%, preferably 1 to 25 wt.-% and particularly preferably 1 to 15 wt.-% of at least one compound according to general formula I,
b) 0.01 to 5 wt.-%, particularly preferably 0.1 to 3.0 wt.-% of at least one initiator for the radical polymerization,
c) 1 to 79.89 wt.-%, preferably 1 to 70 wt.-% and particularly preferably 10 to 70 wt.-% of at least one mono- or multifunctional (meth)acrylate,
d) 20 to 85 wt.-%, preferably 30 to 80 wt.-% and particularly preferably 40 to 75 wt.-% of at least one filler.

Filler-containing compositions are suitable in particular for the production of inlays, onlays, veneers, dental filling materials or as composite materials for stereolithography or 3D printing.

All percentages herein are percentages by weight and relate to the total mass of the material, unless otherwise indicated.

Compositions which consist of the named substances are particularly preferred. Furthermore, those compositions are preferred in which the individual components are in each case selected from the above-named preferred and particularly preferred substances.

It was surprisingly found that compositions which contain the vinyl ethers according to the invention according to Formula I have, after curing, advantageous mechanical properties, such as e.g. an improved impact resistance, a lower shrinkage stress, a higher storage modulus $G'_{(25°\ C.)}$ and a greater elongation at break. These properties are advantageous in particular in the stereolithographic production of shaped bodies or dental prostheses because they guarantee high dimensional stability and breaking strength.

The improved impact resistance of the materials according to the invention is to be emphasized. After polymerization, the compositions preferably have an impact energy of from 3 to 300 kJ/m$^2$, particularly preferably from 5 to 250 kJ/m$^2$ and quite particularly preferably from 10 to 200 kJ/m$^2$. The toughness properties are determined using the DYNSTAT system in accordance with DIN 53435, wherein the impact resistance (impact energy) of unnotched test pieces is determined in the impact bending configuration. For this purpose, sample bars (15×10×4 mm) are produced from the polymerizable compositions and Dynstat Impact Tests are carried out using a 10 kpcm hammer (10 J).

Furthermore, the compositions according to the invention advantageously have a lower shrinkage stress. After polymerization, the compositions preferably have a shrinkage force of from 1 to 60 N, particularly preferably from 3 to 40 N and quite particularly preferably from 3 to 30 N. The shrinkage force is measured according to Watts' method (D. C. Watts et al., Dental Materials 19, 1-11 (2003)) using a universal testing machine. Here, the sample is placed between a steel bar, which is connected to the measuring cell of the testing machine, and a glass plate, which is secured to the stationary part of the testing machine. The surfaces of the steel bar and of the glass plate are pre-treated with a primer, whereby a firm bond is formed between the sample and the two substrates. Finally, the sample is irradiated, which leads to the build-up of a measurable shrinkage force.

In addition, the compositions according to the invention are characterized by an advantageous storage modulus at room temperature $G'_{(25°\ C.)}$ After polymerization, the compositions preferably have a storage modulus at room temperature $G'_{(25°\ C.)}$ of from 0.1 to 20 MPa, particularly preferably from 0.5 to 15 MPa and quite particularly preferably from 0.5 to 10 MPa. The storage modulus at room temperature $G'_{(25°\ C.)}$ is determined in that the polymerizable compositions are poured into silicone moulds and polymerized in a light furnace (e.g. Lumamat 100 model, Ivoclar AG) (e.g. 10 min irradiation with an intensity of approx. 20 mW/cm$^2$). The bars are turned and irradiated again. The sample bars are then ground and measured on an MCR301 rheometer from Anton Paar with a CTD (Convection Temperature Control) oven and an inserted solid rectangular fixture (SRF12 for rectangular cross sections up to 12 mm). The heating rate is set at 2° C./min. All samples are heated up from −100° C. to 200° C. and oscillated with a constant frequency of 1 Hz and 0.1% deflection.

The compositions according to the invention additionally have an improved elongation at break. After polymerization, the compositions preferably exhibit an elongation at break of from 0.5 to 150%, particularly preferably from 1 to 100% and quite particularly preferably from 2 to 80%. The elongation at break is determined by tensile tests. For this, sample bars are made from the polymerizable compositions according to ISO 527 and measured on a Zwick 2050 apparatus, from Zwick. The tests themselves are carried out with a crosshead speed of 5 ram/min.

The compositions according to the invention are further characterized by a reduced glass transition temperature in a narrow temperature range. After polymerization, the compositions preferably have a glass transition temperature of from 10 to 200° C., particularly preferably from 20 to 150° C. and quite particularly preferably from 40 to 150° C. The full width at half maximum of the loss factor curve at glass transition (FWHM) is preferably less than 150° C., particularly preferably less than 100° C. and quite particularly preferably less than 60° C. The glass transition temperature $T_G$ and the full width at half maximum of the loss factor curve at glass transition (FWHM) are determined in that the polymerizable compositions are poured into silicone moulds and polymerized in a light furnace (e.g. Lumamat 100 model, Ivoclar AG) (e.g. 10 min irradiation with an intensity of approx. 20 mW/cm$^2$). The bars are turned and irradiated again. The sample bars are then ground and measured on an MCR301 Anton Paar rheometer with a CTD (Convection Temperature Control) oven and an inserted solid rectangular fixture (SRF12 for rectangular cross sections up to 12 mm). The heating rate is set at 2° C./min. All samples are heated up from −100° C. to 200° C. and oscillated with a constant frequency of 1 Hz and 0.1% deflection.

The materials according to the invention are particularly suitable as dental materials, in particular as dental cements, filling composites, veneering materials, coating materials and adhesives as well as materials for the production of prostheses, artificial teeth, inlays, onlays, crowns and bridges.

The dental materials are suitable primarily for intraoral application by the dentist for the restoration of damaged teeth, i.e. for therapeutic application, e.g. as dental cements, filling composites and veneering materials. However, they can also be used extraorally, for example in the production or repair of dental restorations, such as prostheses, artificial teeth, inlays, onlays, crowns and bridges.

A further subject-matter of the invention are homo- and co-polymers which can be obtained by polymerization of compositions according to the invention. Polymers of this type can be processed to form prostheses or artificial teeth using machining processes, for example. They are preferably available in the form of cylindrical or disc-shaped blanks.

The polymer materials according to the invention are also suitable for the production of shaped bodies for dental, but also for non-dental purposes, which can be produced e.g. by means of casting, compression moulding and in particular by generative processes such as 3D printing.

The materials according to the invention are further suitable as medical materials for the production of medical products for surgery, such as e.g. as materials for the production of implants for hearing prostheses, cartilage or bone replacements, and for ophthalmology, such as e.g. as materials for the production of intraocular lenses.

The invention also relates to the use of compounds of Formula I as chain transfer agents in radical polymerization or to control or regulate the network structure in the polymerization in particular of (meth)acrylates.

The invention is explained in more detail in the following with reference to examples.

Embodiment Examples

Example 1

Synthesis of 2-((1-ethoxy-2-methyl-1-oxopropan-2-yl)oxy)acrylic acid ethyl ester (1)

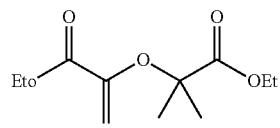

1$^{st}$ Stage: Synthesis of 2-(2-ethoxy-2-oxoethoxy)-2-methylpropanoic acid ethyl ester (ZP-1)

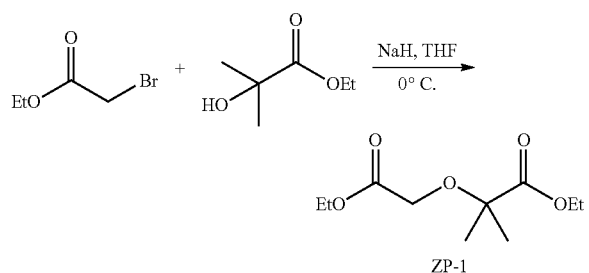

One equivalent of a 60% sodium hydride mixture (137.5 mmol, 5.48 g) in mineral oil was placed in 300 ml dry tetrahydrofuran (THF), cooled to 0° C. and the apparatus was flushed with argon. Ethyl 2-hydroxyisobutyrate (137.5 mmol, 18.17 g) was slowly added dropwise and stirred at 0° C. until gas formation could no longer be detected (approx. 1 h). Then ethyl bromoacetate (137.5 mmol, 22.95 g) was added dropwise and stirred overnight at room temperature. The reaction was terminated through the addition of 100 ml saturated NH$_4$Cl solution, the aqueous phase was extracted three times with 150 ml ethyl acetate and the combined organic phase was dried over anhydrous Na$_2$SO$_4$. The solvent was removed and the crude product was purified by means of high vacuum distillation (boiling point: 70° C. at 0.07 mbar). The product ZP1 could be obtained in a yield of 19.4 g (65% of theoretical yield) as a colourless liquid.

Rf value: 0.5 (petroleum ether (PE):ethyl acetate (EA) 5:1).

$^1$H-NMR: (400 MHz, CDCl$_3$) δ (ppm): 4.20 (4H, m, —CH$_2$—CH$_3$), 4.10 (2H, s, —CH$_2$—O—), 1.47 (6H, s, —C—CH$_3$), 1.27 (6H, t, —CH$_2$—CH$_3$, J=7.1 Hz).

$^{13}$C-NMR: (100 MHz, CDCl$_3$) δ (ppm): 174.0 (C=O), 170.4 (C=O), 78.5 (C4), 63.3 (C2), 61.3 (C2), 61.0 (C2), 24.6 (C1), 14.3 (C1).

2nd Stage: Synthesis of 2-((1-ethoxy-2-methyl-1-oxopropan-2-yl)oxy)-3-hydroxypropanoic acid ethyl ester (ZP-2)

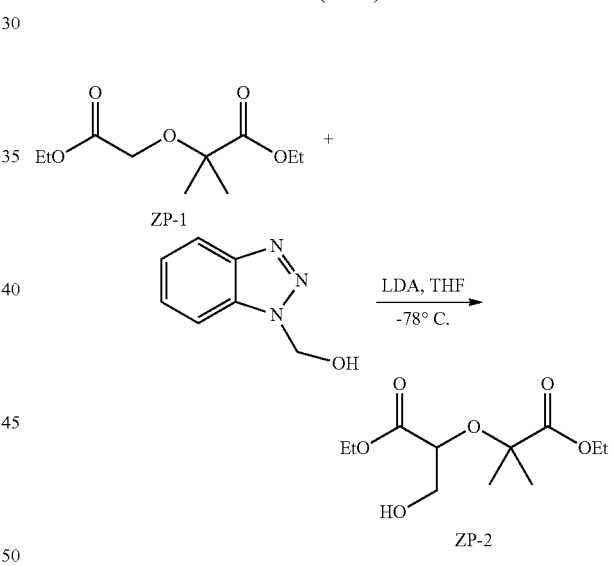

The reaction was carried out in a 1000 ml three-neck flask under an argon atmosphere. 3 equivalents n-butyllithium (137.5 mmol, 55 ml 2.5 M in hexane) were placed in 250 ml dry tetrahydrofuran (THF) and cooled to −10° C. 3.5 equivalents dry diisopropylamine (160.3 mmol, 16.2 g) were added dropwise and the reaction solution was stirred for 30 min at 0° C. Then, the reaction solution was cooled to −78° C. and a solution of (2-(2-ethoxy-2-oxoethoxy)-2-methylpropanoic acid ethyl ester from Stage 1 (14.5 mmol, 3.59 g) in 60 ml THF was slowly added dropwise. Finally, the reaction solution was stirred for 1 h at −78° C., benzotriazole-1-methanol (91.6 mmol, 13.7 g) dissolved in 250 ml THF was slowly added dropwise and the reaction solution was then stirred for 2 h at −78° C. The reaction was terminated through the addition of 150 ml saturated NH$_4$Cl solution and the aqueous phase was extracted three times with 200 ml diethyl ether in each case. The combined organic phase was washed with 150 ml each of 4N NaOH and saturated salt solution, wherein the washing step with 4N NaOH was carried out as quickly as possible. The organic phase was dried over anhydrous $Na_2SO_4$ and the crude product was obtained as a yellow oil in a yield of 7.70 g (77% of theoretical yield) after evaporating off the solvent. The crude product was purified by means of column chromatography (petroleum ether (PE):ethyl acetate (EA) 5:1→3:2) and the intermediate product ZP-2 was obtained in a yield of 3.59 g (36% of theoretical yield).

Rf value: 0.3 (PE:EA 3:1).

$^1$H-NMR: (400 MHz, $CDCl_3$) δ (ppm): 4.20 (5H, m, —$CH_2$—$CH_3$, O—CH—), 3.84 (2H, m, —$CH_2$—OH), 1.51 (3H, s, —C—$CH_3$), 1.44 (3H, s, —C—$CH_3$), 1.27 (6H, t, —$CH_2$—$CH_3$, J=7.1 Hz).

$^{13}$C-NMR: (100 MHz, $CDCl_3$) δ (ppm): 175.4 (C=O), 171.4 (C=O), 79.0 (C4), 76.2 (C3), 64.3 (C2), 61.8 (C2), 61.3 (C2), 27.3 (C1), 22.7 (C1), 14.3 (C1), 14.3 (C1).

3$^{rd}$ Stage: Synthesis of 2-((1-ethoxy-2-methyl-1-oxopropan-2-yl)oxy)acrylic acid ethyl ester (1)

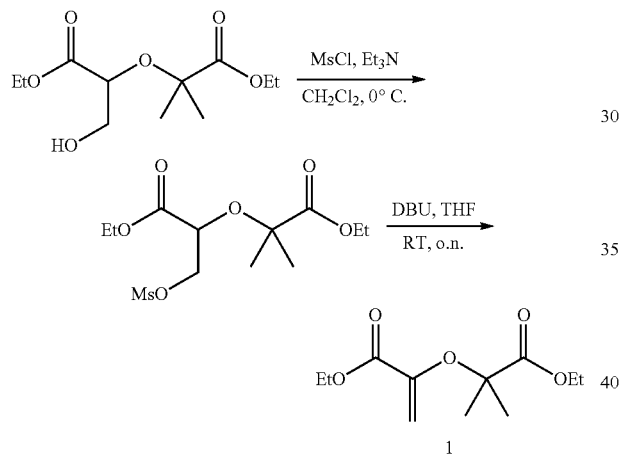

1

ZP-2 (14.5 mmol, 3.59 g) was placed in 45 ml dry dichloromethane under an argon atmosphere, the solution was cooled to 0° C. and 1.3 equivalents triethylamine (18.8 mmol, 1.90 g) were added. Then 1.2 equivalents mesyl chloride (17.4 mmol, 1.99 g) were added dropwise and the solution was stirred for 1 h at room temperature. The reaction was terminated through the addition of 30 ml saturated $NaHCO_3$ solution and the aqueous solution was extracted three times with 30 ml dichloromethane. After the solvent had been removed, the crude product was dissolved in dry tetrahydrofuran (THF), placed under an argon atmosphere and cooled to 0° C. 3 equivalents diazabicycloundecene (DBU, 43.4 mmol, 8.60 g) were added and the reaction solution was stirred overnight at room temperature. The reaction was terminated through the addition of 20 ml water, the aqueous phase was extracted three times with 20 ml dichloromethane in each case and dried over anhydrous $Na_2SO_4$. The solvent was removed and produced the crude product as a colourless oil. The excess DBU could be removed by means of column chromatography (eluent petroleum ether (PE):ethyl acetate (EA) 10:1) and the pure product 1 was obtained in a yield of 2.32 g (70% of theoretical yield).

Rf value: 0.4 (PE:EA 10:1)

$^1$H-NMR: (400 MHz, $CDCl_3$) δ (ppm): 5.53 (1H, d, C=$CH_2$, J=2.7 Hz), 4.55 (1H, d, C=$CH_2$, J=2.7 Hz), 4.22 (4H, qq, —$CH_2$—$CH_3$), 1.59 (6H, s, —C—$CH_3$), 1.29 (6H, 2 t, —$CH_2$—$CH_3$).

$^{13}$C-NMR: (100 MHz, $CDCl_3$) δ (ppm): 173.4 (C=O), 163.7 (C=O), 147.9 (C4), 100.3 (C2), 79.7 (C4), 61.6 (C2), 24.6 (C1), 14.3 (C1), 14.3 (C1).

Example 2

Synthesis of 2,2-dimethyl-4-methyleneglutaric acid dimethyl ester (2) (Reference Compound)

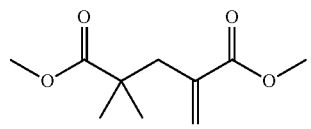

2

The synthesis of reference compound (2) was carried out analogously to Moad et al. (Moad, C. L.; Moad, G.; Rizzardo, E.; Thang, S. H., Chain Transfer Activity of ω-Unsaturated Methyl Methacrylate Oligomers. *Macromolecules* 1996, 29 (24), 7717-7726).

Example 3

Synthesis of bis(2-hydroxy-3-(methacryloyloxy) propyl)-2,2-dimethyl-4-methylenepentanedioate (3) (Reference Compound)

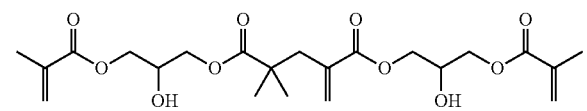

3

The synthesis of compound (3) was carried out analogously to WO 2012/112350 A2.

Example 4

Synthesis of 2-({1-[2-(methacryloyloxy)ethoxy]-2-methyl-1-oxopropan-2-yl}oxy)acrylic acid 2-(methacryloyloxy)ethyl ester (4)

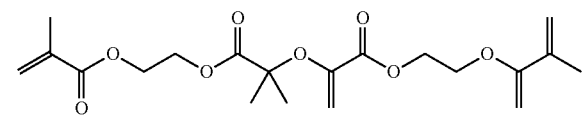

4

1st Stage: 2-[(2-carboxypropan-2-yl)oxy]acrylic acid
(ZP-3)

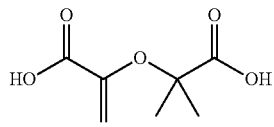

2-[(1-Ethoxy-2-methyl-1-oxopropan-2-yl)oxy]acrylic acid ethyl ester 1 (3.06 g; 13.3 mmol) was added to a solution of potassium hydroxide (2.09 g; 37.2 mmol) in water (30 ml) and the mixture was heated for 24 h at 90° C. After cooling, the reaction solution was acidified using hydrochloric acid (2N) (pH=1) and extracted with tert-butyl methyl ether (4×50 ml). The combined organic phases were dried over anhydrous sodium sulphate, filtered and concentrated on a rotary evaporator. 2.29 g ZP-3 (13.1 mmol; 99% yield) was obtained as a yellow oil.

$^1$H-NMR (CDCl$_3$, 400 MHz): δ=10.17 (s, 2H; OH), 5.83 (d, 1H; J=2.5 Hz; =CH), 4.93 (d, 1H; J=2.5 Hz; =CH), 1.62 (s, 6H; CH$_3$).

$^{13}$C-NMR (CDCl$_3$, 100.6 MHz): δ=176.0 (C=O), 167.3 (C=O), 146.2 (=C), 105.4 (=CH$_2$), 80.3 (C), 24.2 (CH$_3$).

2$^{nd}$ Stage: 2-({1-[2-(methacryloyloxy)ethoxy]-2-methyl-1-oxo-propan-2-yl}oxy)acrylic acid 2-(methacryloyloxy)ethyl ester (4)

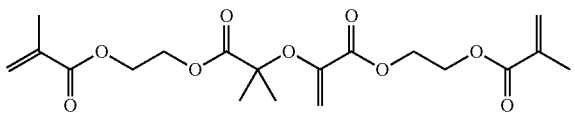

A solution of 2-[(2-carboxypropan-2-yl)oxy]acrylic acid ZP-3 (2.19 g; 12.6 mmol), 2-hydroxyethyl methacrylate (3.44 g, 26.4 mmol), N,N-dimethylaminopyridine (0.24 g; 2.0 mmol) and 2,6-di-tert-butyl-4-methylphenol (10 mg) in dichloromethane (100 ml) was cooled to 0° C. and N-(3-dimethylaminopropyl)-N'-ethylcarbodiimide hydrochloride (5.30 g; 27.7 mmol) was added in portions. The reaction mixture was stirred for 2 h with ice-cooling and then at ambient temperature. After 20 h, the solution was diluted with n-heptane (100 ml) and filtered through a layer of silica gel. The filtrate was concentrated on a rotary evaporator. The crude product was purified by means of column chromatography (SiO$_2$, n-heptane/ethyl acetate 3:1; R$_f$=0.3). 2.39 g of 4 (6.0 mmol; 48% yield) was obtained as a yellowish oil.

$^1$H-NMR (CDCl$_3$, 400 MHz): δ=6.13 (m, 1H; =CH), 6.10 (m, 1H; =CH), 5.59 (m, 2H; =CH), 5.56 (d, 1H; J=2.5 Hz; =CH), 4.64 (d, 1H; J=2.5 Hz; =CH), 4.40 (m, 8H; CH$_2$), 1.95 (m, 3H; CH$_3$), 1.93 (m, 3H; CH$_3$), 1.59 (s, 6H; CH$_3$).

$^{13}$C-NMR (CDCl$_3$, 100.6 MHz): δ=172.8 (C=O), 166.8 (C=O), 166.7 (C=O), 162.9 (C=O), 147.0 (=C), 135.7 (=C), 135.7 (=C), 125.9 (=CH$_2$), 125.9 (=CH$_2$), 101.3 (=CH$_2$), 79.5 (C), 62.8 (CH$_2$), 62.7 (CH$_2$), 61.9 (CH$_2$), 61.9 (CH$_2$), 24.2 (CH$_3$), 18.0 (CH$_3$), 18.0 (CH$_3$).

Example 5

Reactivity Measurements with Benzyl Methacrylate

In order to investigate the polymerization reactivity and regulatability of the compounds according to the invention, formulations were prepared with the monofunctional monomer benzyl methacrylate (BMA) and 20 double-bond percent (DB %) of the transfer reagent relative to the total quantity of double bonds in the formulation. As transfer reagent, (1) according to Example 1 was compared with (2) from Example 2. 1 mol % bis(4-methoxybenzoyl)diethylgermanium (BMDGe) was also added to all formulations as photoinitiator. For the polymerization, a Netzsch DSC 204 F1 Phoenix® differential scanning calorimeter (DSC) with autosampler (Netzsch-Gerätebau GmbH) was used. The measurements were carried out isothermally at 25° C. under a nitrogen atmosphere. 10±1 mg sample formulation was weighed into an aluminium DSC pan which was placed in the DSC chamber using the autosampler. The sample was flushed with nitrogen for 4 min (20 ml/min) and then irradiated for 5 min using filtered UV light (broadband Hg light source EXFO Omnicure 2000 from Excelitas) in the visible range of from 400-500 nm with an intensity of 1 W/cm$^2$ at the beam output of the lamp. The time taken to reach 95% of the maximum conversion (t$_{95}$) and the time taken to reach the maximum rate of polymerization (t$_{max}$) were used to evaluate the reactivity.

The polymerized samples were dissolved in tetrahydrofuran (THF) and analyzed using gel permeation chromatography (GPC) with a Waters GPC with three columns connected in series (Styragel HR 0.5, Styragel HR 3 and Styragel HR 4) and a Waters 2410 RI detector in a column oven at 40° C. and with a flow rate of 1.0 ml/min. Polystyrene standards were used for the calibration. The ratio between the number-average molecular weight of the polymer regulated with transfer reagent and that of pure poly-BMA (Mn$_{mod}$/Mn$_{BMA}$) shows how far the average molecular weight is reduced by the transfer reagent. The polydispersity index (PDI) indicates the distribution of molar mass in the polymers obtained. For a successful regulation, a significant reduction in the molecular weight, i.e. a low value for the ratio Mn$_{mod}$/Mn$_{BMA}$, and for the PDI, accompanied by a high rate of polymerization, i.e. relatively low values for t$_{95}$ and t$_{max}$, is sought. In Table 1, comparison test V1 is the polymerization of pure monofunctional methacrylate BMA without transfer reagent. In test B1, a mixture of BMA and transfer reagent (1) according to the invention was used, while in comparison test V2, a mixture of BMA and the reference transfer reagent (2) was investigated.

TABLE 1

Results of the reactivity measurements with transfer reagent (1) and reference compound (2)

| Regulator | Example | $t_{95}$ [s] | $t_{max}$ [s] | $DBC_{BMA}$// $DBC_{regulator}$ [%]//[%] | $M_n$ [kDa] | $Mn_{mod}$/ $Mn_{BMA}$ | PDI |
|---|---|---|---|---|---|---|---|
| — | V1 | 98 | 18.9 | 58//— | 3.6 | — | 3.4 |
| 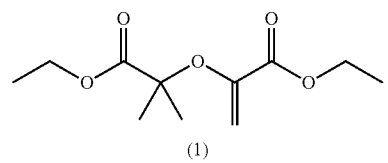 [SMILES: C=C(OC(C)(C)C(=O)OCC)C(=O)OCC] (1) | B1 | 127 | 17.1 | 50//30 | 1.2 | 0.33 | 1.9 |
| 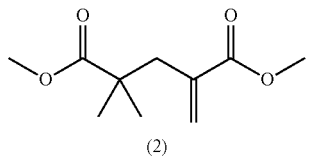 (2) | V2 | 125 | 16.9 | 24//12 | 1.4 | 0.39 | 2.3 |

Table 1 shows that, when compound (1) is used as transfer reagent according to the invention, both $t_{95}$ and $t_{max}$ are increased compared with pure BMA in comparison example 1, wherein compound (2) in comparison example 2 also shows this retardation to a similar degree. If, however, the double-bond conversion (DBC) of BMA and of the transfer reagent is observed, it can be seen very clearly that the mixture with transfer reagent (1) has significantly higher conversions than the mixture with reference compound (2) and thus meets the demands on a transfer reagent better. This also becomes clear on observing the ratio of the number average $M_n$ between regulated and unregulated poly(BMA). While in the case of V2 with reference compound (2) the low molecular weight can be explained by the very low conversion, in the case of B1 with transfer reagent (1) both a low molecular weight and a reasonable double-bond conversion are obtained.

Example 6

Reactivity Measurements for Polymer Materials with Dimethacrylates

In order to likewise investigate the reactivity of compound (1) according to the invention in an applied polymer matrix, photo-DSC measurements were carried out for polymer materials with difunctional methacrylates. The investigations were carried out under the same conditions as in Example 5 with a Netzsch DSC 204 F1 Phoenix® differential scanning calorimeter (DSC) with autosampler (Netzsch-Gerätebau GmbH). An equimolar mixture of the commercially available dimethacrylates urethane dimethacrylate (UDMA, isomer mixture; CAS: 72869-86-4) and 1,10-decanediol dimethacrylate ($D_3MA$) (resin mixture, 2M) was used as polymer matrix without transfer reagent. Compound (1) according to the invention and reference compound (2) were again used as transfer reagent, wherein in addition compound (3) known from WO 2012/112350 A2 was also investigated. 20 double-bond percent (DB %) of the respective transfer reagent (1) and (2) was added to the base mixture relative to the total quantity of double bonds in the formulation. In addition, a mixture of the base matrix with 0.20 molar equivalents of compound (3) was prepared.

TABLE 2

Results of the reactivity measurements with transfer reagent (1) and reference compounds (2) and (3)

| Compound | Example | $t_{95}$ [s] | $t_{max}$ [s] | DBC [%] |
|---|---|---|---|---|
| No transfer reagent (only UDMA/$D_3$MA) | V3 | 45.2 | 4.2 | 67 |
| 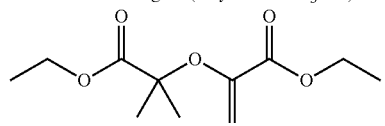 (1) | B2 | 105.0 | 14.5 | 87 |
| 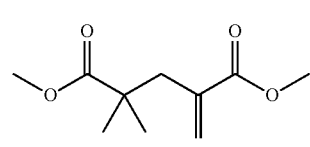 (2) | V4 | 129 | 15.4 | 39 |

TABLE 2-continued

Results of the reactivity measurements with transfer reagent (1) and reference compounds (2) and (3)

| Compound | Example | $t_{95}$ [s] | $t_{max}$ [s] | DBC [%] |
|---|---|---|---|---|
| 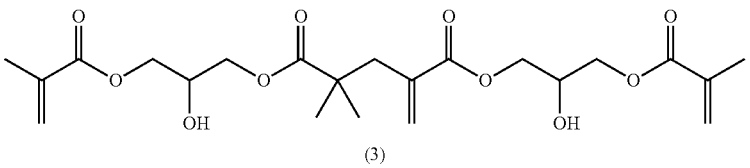 [SMILES: C=C(C)C(=O)OCC(O)COC(=O)C(=C)CC(C)(C)C(=O)OCC(O)COC(=O)C(=C)C] (3) | V5 | 85.2 | 14.3 | 67 |

It can be seen from Table 2 that, when used as transfer reagent according to the invention (test B2), compound 1 not only increases the time taken to reach the maximum rate of polymerization ($t_{max}$) and the time taken to reach 95% conversion ($t_{95}$) compared with comparison test V3 without transfer reagent, but also brings about an increase in the double-bond conversion to 87% (67% in V3). In comparison test V4 with reference compound (2), the significant increase in $t_{max}$ and $t_{95}$ is also seen, but here it is even more pronounced than in B2. However, here the double-bond conversion is also greatly reduced to only 39%. Thus, reference compound (2) only has a retarding effect in the polymer matrix while, although compound (1) slows down the system somewhat, it regulates it effectively and increases the conversion. Although the addition of hybrid monomer 3 in comparison test V5 results in a considerable retardation of the system, it does not result in an increase in the double-bond conversion, compared with V3. It can consequently be assumed that reference compound (3) only reacts as a comonomer rather than regulating the polymerization through chain transfer.

Example 7

Preparation and Characterization of Dimethacrylate Photopolymers with an RT-NIR Photorheometer In a manner similar to the preceding examples, polymer materials consisting of an equimolar mixture of UDMA and D₃MA (comparison example 6) and the respective transfer reagent were prepared. 20 double-bond percent (DB %) each of compound (1) (Example 3), reference compound (2) (comparison example 7) and 0.2 molar equivalents of compound (3) (comparison example 8) were added to the UDMA-D₃MA base matrix relative to the total quantity of double bonds in the formulation. 1 wt.-% bis(4-methoxybenzoyl)diethylgermanium (BMDGe, Ivocerin®) was also added to all formulations as photoinitiator. To check the photoreactivity, the prepared formulations were measured using an MCR302 WESP real-time near-infrared (RT-NIR) photorheometer from Anton Paar, which was coupled to a Bruker Vertex-80 IR spectrometer to monitor conversion. A PP-25 measuring system was used and the measuring gap was adjusted to 0.2 mm. Before and during curing (10 mW/cm² on sample surface; 400-500 nm; Omnicure 2000 UV lamp), the storage and loss modulus of the samples were measured in oscillation mode (1% deflection, 1 Hz). At the same time, IR spectra of the sample were recorded during the measurement at a frequency of ~5 Hz. The reaching of the gel point (intersection of storage and loss modulus) and the time taken to reach 95% of the final storage modulus ($t_{95\%}$) were used as a measure of the photoreactivity. In addition, the conversion at the gel point ($DBC_g$), the total conversion (DBC) and the photopolymerization-induced shrinkage stress ($F_S$) were determined. The results obtained are summarized in Table 3.

TABLE 3

RT-NIR photorheometry

| Example | Compound | Gel point [s] | $DBC_g$ [%] | DBC [%] | $t_{95\%}$ [s] | $F_s$ [N] |
|---|---|---|---|---|---|---|
| V6 | — | 1.3 | 17 | 79 | 41 | −41 |
| B3 | (1)[a] | 15.3 | 31 | 91 | 202 | −26 |
| V7 | (2)[b] | 54.3 | 17 | 43 | 279 | −15 |
| V8 | (3)[c] | 8.5 | 10 | 65 | 93 | −28 |

[a] = 2-((1-ethoxy-2-methyl-1-oxopropan-2-yl)oxy)acrylic acid ethyl ester
[b] = 2,2-dimethyl-4-methyleneglutaric acid dimethyl ester
[c] = bis(2-hydroxy-3-(methacryloyloxy)propyl)-2,2-dimethyl-4-methylenepentanedioate The results in Table 3 show that the addition of both transfer reagents (1) and (2) leads in each case to a delay in the gel point. In addition, in the case of compound (1) according to the invention, both the conversion at the gel point (31%) and the final double-bond conversion (91%) were considerably increased, while reference compound (2) caused no difference in the conversion at the gel point and even a considerable reduction in the final conversion. Despite the increased conversion, compound 1 is characterized by a significantly weaker polymerization-induced shrinkage stress, while the low shrinkage stress in the case of V7 arises from the significantly lower conversion. The advantageousness of transfer reagent (1) compared with transfer reagent (2) known from the literature can thus also be seen here. Although in V8 reference compound (3) increases the time to the gel point, like compound (2) it also results in a considerable reduction in the conversion at the gel point and also in a lower final conversion (65%). Although the resulting shrinkage force is lower than in the case of V6, as in V7 this is to be attributed to the lower conversion and again shows the poor action as transfer reagent.

Example 8

Dynamic Mechanical Thermal Analysis (DMTA) of the Photopolymers Prepared

To investigate the glass transition, formulations prepared analogously to the above test B3 and comparison tests V6, V7 and V8 were poured into silicone moulds and polymerized in a light furnace (Lumamat 100 model, Ivoclar AG) using program 2 (10 min irradiation with an intensity of approx. 20 mW/cm²). The bars were turned and cured again. The sample bars were ground and then measured on an MCR301 rheometer from Anton Paar with a CTD (Convection Temperature Control) oven and an inserted solid rectangular fixture (SRF12 for rectangular cross sections up to 12 mm). The heating rate was set at 2° C./min. All samples were heated up from −100° C. to 200° C. and oscillated with a constant frequency of 1 Hz and 0.1% deflection. In Table 4 below, the results for the determination of the storage modulus at room temperature (G'$_{(25°\,C.)}$), the glass transition temperature (T$_G$) and the full width at half maximum of the loss factor curve at glass transition (FWHM) are given.

TABLE 4

Results of the DMTA

| Example | Compound | G'$_{(25°\,C.)}$ [MPa] | T$_G$ [° C.] | FWHM [° C.] |
|---|---|---|---|---|
| V9 | — | 1550 | 156 | 161 |
| B4 | (1)$^a$ | 840 | 57 | 14 |
| V10 | (2)$^b$ | 379 | 60 | 55 |
| V11 | (3)$^c$ | 1510 | 153 | 168 |

$^a$= 2-((1-ethoxy-2-methyl-1-oxopropan-2-yl)oxy)acrylic acid ethyl ester
$^b$= 2,2-dimethyl-4-methyleneglutaric acid dimethyl ester
$^c$= bis(2-hydroxy-3-(methacryloyloxy)propyl)-2,2-dimethyl-4-methylenepentanedioate The data shown in Table 4 prove that both a lower and a considerably narrower glass transition range are achieved with compound (1) according to the invention as transfer reagent. This trend can also be established in comparison example V10 with reference compound (2) but not by far as significantly as in B4 and at the same time with a much greater drop in the storage modulus at room temperature. Here too can be seen the advantageous properties of polymer materials according to the invention with compound (1) compared with the state of the art. If V11 with reference compound (3) is observed, it can be seen that there was no significant change of the parameters compared with V9 without transfer reagent and thus again the lack of action as transfer reagent and the action merely as a comonomer can be seen.

Example 9

Measurement of the Impact Resistance (Dynstat Impact Test)

The toughness properties were determined using the DYNSTAT system in accordance with DIN 53435, wherein the impact resistance (impact energy) of unnotched test pieces was determined in the impact bending configuration. For this purpose, sample bars (15×10×4 mm) were produced from formulations analogous to the above Example 3 according to the invention and comparison examples 6, 7 and 8 and Dynstat Impact Tests were carried out using a 10 kpcm hammer (10 J). The values obtained are listed in Table 5 below.

TABLE 5

Results of the impact resistance measurements

| Example | Compound | Impact energy [kJ/m$^2$]$^a$ |
|---|---|---|
| V12 | — | 5.9 ± 2.3 |
| B5 | (1)$^b$ | 12.9 ± 2.3 |
| V13 | (2)$^c$ | 6.1 ± 2.1 |
| V14 | (3)$^d$ | 7.7 ± 2.5 |

$^a$= Normalized to width and thickness
$^b$= 2-((1-ethoxy-2-methyl-1-oxopropan-2-yl)oxy)acrylic acid ethyl ester
$^c$= 2,2-dimethyl-4-methyleneglutaric acid dimethyl ester
$^d$= bis(2-hydroxy-3-(methacryloyloxy)propyl)-2,2-dimethyl-4-methylenepentanedioate It can be seen that a considerable increase in impact resistance could only be achieved with compound (1) according to the invention in B5, while, although reference compounds (2) and (3) in V13 and V14 increase the impact resistance, the increase lies within the margin of error. This again proves the advantageous mechanical properties of the polymer materials according to the invention compared with the state of the art.

Example 10

Tensile Test with Photopolymers

In order to obtain further mechanical characteristic data (maximum tensile stress and elongation at break), tensile tests were carried out. For this, sample bars were made in accordance with ISO 527 from formulations analogous to the above Example B3 according to the invention and comparison examples V6, V7 and V8 and measured on a Zwick 2050 apparatus, from Zwick. The tests themselves were carried out with a crosshead speed of 5 mm/min.

TABLE 6

Results of the tensile tests

| Example | Compound | Maximum tensile stress [MPa] | Elongation at break [%] |
|---|---|---|---|
| V15 | — | 66.4 ± 5.4 | 7.7 ± 0.8 |
| B6 | (1)$^a$ | 31.0 ± 1.0 | 26.9 ± 2.8 |
| V16 | (2)$^b$ | 21.8 ± 2.7 | 11.5 ± 2.9 |
| V17 | (3)$^c$ | 68.7 ± 4.3 | 7.98 ± 1.2 |

$^a$= 2-((1-ethoxy-2-methyl-1-oxopropan-2-yl)oxy)acrylic acid ethyl ester
$^b$= 2,2-dimethyl-4-methyleneglutaric acid dimethyl ester
$^c$= bis(2-hydroxy-3-(methacryloyloxy)propyl)-2,2-dimethyl-4-methylenepentanedioate The results in Table 6 show that although the use according to the invention of compound (1) results in a reduction in the maximum tensile stress, the elongation at break is increased by 350%. Reference compound (2) reduces the maximum tensile stress even more significantly and at the same time increases the elongation at break only marginally. In this respect too, compound (1) clearly makes advantageous mechanical properties possible compared with comparison compound (2). As previously, reference compound (3) shows significant changes neither in maximum tensile stress nor in elongation at break.

The invention claimed is:
1. Radically polymerizable composition comprising at least one vinyl ether according to general formula I:

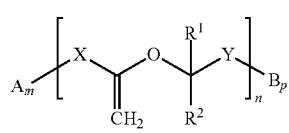

Formula I in which the variables have the following meanings:
A H, CN, a cycloaliphatic, linear or branched aliphatic C$_1$-C$_{30}$ hydrocarbon residue, which can be substituted by one or more substituents, which can be interrupted by one or more urethane groups, ester groups, O and/or S and which can contain 1 to 4 benzene groups,
an aromatic C$_6$-C$_{30}$ hydrocarbon residue, which can be substituted by one or more substituents, wherein the hydrocarbon residues can bear a polymerizable group terminally;

X —COO—, —CON(R³)— or is dispensed with, wherein the bonding to A is effected via O or N;
B H, CN, a cycloaliphatic, linear or branched aliphatic $C_1$-$C_{30}$ hydrocarbon residue, which can be substituted by one or more substituents, which can be interrupted by one or more urethane groups, ester groups, O and/or S and which can contain 1 to 4 benzene groups,
an aromatic $C_6$-$C_{30}$ hydrocarbon residue, which can be substituted by one or more substituents, wherein the hydrocarbon residues can bear a polymerizable group terminally;
Y —COO—, —CON(R³)— or is dispensed with, wherein the bonding to B is effected via O or N;
$R^{1-3}$ in each case independently of one another hydrogen, a cycloaliphatic, linear or branched aliphatic $C_1$-$C_{10}$ hydrocarbon residue, which can be interrupted by one or more oxygen atoms and which can be substituted by one or more OH groups, or
an aromatic $C_6$-$C_{10}$ hydrocarbon residue, which can be substituted by one or more OH groups;
m an integer from 1 to 6;
n an integer from 1 to 6;
p an integer from 1 to 6; wherein
m and p cannot be greater than 1 at the same time and wherein if m=1, p=n, and if p=1, m=n.

2. The composition according to claim 1, in which the vinyl ether is a compound of Formula II,

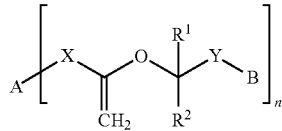

Formula II in which the variables have the following meanings:
A H, CN, a cycloaliphatic, linear or branched aliphatic $C_1$-$C_{30}$ hydrocarbon residue, which can be substituted by one or more substituents, which can be interrupted by one or more urethane groups, ester groups, O and/or S and which can contain 1 to 4 benzene groups,
an aromatic $C_6$-$C_{30}$ hydrocarbon residue, which can be substituted by one or more substituents, wherein the hydrocarbon residues can bear a polymerizable group terminally;
X —COO—, —CON(R³)— or is dispensed with, wherein the bonding to A is effected via O or N;
B H, CN, a cycloaliphatic, linear or branched aliphatic $C_1$-$C_{30}$ hydrocarbon residue, which can be substituted by one or more substituents, which can be interrupted by one or more urethane groups, ester groups, O and/or S and which can contain 1 to 4 benzene groups, an aromatic $C_6$-$C_{30}$ hydrocarbon residue, which can be substituted by one or more substituents, wherein the hydrocarbon residues can bear a polymerizable group terminally;
Y —COO—, —CON(R³)— or is dispensed with, wherein the bonding to B is effected via O or N;
$R^{1-3}$ in each case independently of one another hydrogen, a cycloaliphatic, linear or branched aliphatic $C_1$-$C_{10}$ hydrocarbon residue, which can be interrupted by one or more oxygen atoms and which can be substituted by one or more OH groups, or an aromatic $C_6$-$C_{10}$ hydrocarbon residue, which can be substituted by one or more OH groups;
n an integer from 1 to 6.

3. The composition according to claim 2, in which the variables of Formula II have the following meanings:
A cycloaliphatic, linear or branched aliphatic $C_1$-$C_{12}$ hydrocarbon residue, which can be substituted by 1 to 6 substituents, which can be interrupted by 1 to 2 urethane groups, ester groups, O and/or S and which can contain 1 to 2 benzene groups, an aromatic $C_6$-$C_{14}$ hydrocarbon residue, which can be substituted by 1 to 6 substituents, wherein the hydrocarbon residues can bear a polymerizable group;
X —COO—, —CON(R³)— or is dispensed with, wherein the bonding to A is effected via O or N;
B cycloaliphatic, linear or branched aliphatic $C_1$-$C_{12}$ hydrocarbon residue, which can be interrupted by 1 to 2 urethane groups, ester groups, O and/or S and which can contain 1 to 2 benzene groups,
an aromatic $C_6$-$C_{14}$ hydrocarbon residue, which can be substituted by 1 to 6 substituents, wherein the hydrocarbon residues can bear a polymerizable group;
Y —COO—, —CON(R³)— or is dispensed with, wherein the bonding to B is effected via O or N;
$R^{1-3}$ in each case independently of one another hydrogen, a cycloaliphatic, linear or branched aliphatic $C_1$-$C_6$ hydrocarbon residue, which can be interrupted by 1 to 2 oxygen atoms and which can be substituted by 1 to 4 OH groups, or
an aromatic $C_6$-$C_{10}$ hydrocarbon residue, which can be substituted by 1 to 4 OH groups;
n an integer from 1 to 3.

4. The composition according to claim 1, in which the vinyl ether is a compound of Formula III,

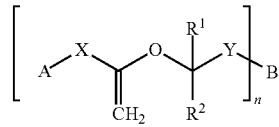

Formula III in which the variables have the following meanings:
A H, CN, a cycloaliphatic, linear or branched aliphatic $C_1$-$C_{30}$ hydrocarbon residue, which can be substituted by one or more substituents, which can be interrupted by one or more urethane groups, ester groups, O and/or S and which can contain 1 to 4 benzene groups,
an aromatic $C_6$-$C_{30}$ hydrocarbon residue, which can be substituted by one or more substituents, wherein the hydrocarbon residues can bear a polymerizable group terminally;
X —COO—, —CON(R³)— or is dispensed with, wherein the bonding to A is effected via O or N;
B H, CN, a cycloaliphatic, linear or branched aliphatic $C_1$-$C_{30}$ hydrocarbon residue, which can be substituted by one or more substituents, which can be interrupted by one or more urethane groups, ester groups, O and/or S and which can contain 1 to 4 benzene groups,
an aromatic $C_6$-$C_{30}$ hydrocarbon residue, which can be substituted by one or more substituents, wherein the hydrocarbon residues can bear a polymerizable group terminally;
Y —COO—, —CON(R³)— or is dispensed with, wherein the bonding to B is effected via O or N;
$R^{1-3}$ in each case independently of one another hydrogen, a cycloaliphatic, linear or branched aliphatic $C_1$-$C_{10}$ hydrocarbon residue, which can be interrupted by one or more oxygen atoms and which can be substituted by one or more OH groups, or an aromatic $C_6$-$C_{10}$ hydrocarbon residue, which can be substituted by one or more OH groups;

n an integer from 1 to 6.

5. The composition according to claim 4, in which the variables of Formula III have the following meanings:

A cycloaliphatic, linear or branched aliphatic $C_1$-$C_{12}$ hydrocarbon residue, which can be substituted by 1 to 6 substituents, which can be interrupted by 1 to 2 urethane groups, ester groups, O and/or S and which can contain 1 to 2 benzene groups, an aromatic $C_6$-$C_{14}$ hydrocarbon residue, which can be substituted by 1 to 6, substituents, wherein the hydrocarbon residues can bear a polymerizable group, terminally;

X —COO—, —CON($R^3$)— or is dispensed with, wherein the bonding to A is effected via O or N;

B cycloaliphatic, linear or branched aliphatic $C_1$-$C_{12}$ hydrocarbon residue, which can be interrupted by 1 to 2 urethane groups, ester groups, O and/or S and which can contain 1 to 2 benzene groups, an aromatic $C_6$-$C_{14}$ hydrocarbon residue, which can be substituted by 1 to 6, wherein the hydrocarbon residues can bear a polymerizable group, terminally;

Y —COO—, —CON($R^3$)— or is dispensed with, wherein the bonding to B is effected via O or N;

$R^{1-3}$ in each case independently of one another hydrogen, a cycloaliphatic, linear or branched aliphatic $C_1$-$C_6$ hydrocarbon residue, which can be interrupted by 1 to 2 oxygen atoms and which can be substituted by 1 to 4 OH groups, or an aromatic $C_6$-$C_{10}$ hydrocarbon residue, which can be substituted by 1 to 4 OH groups;

n an integer from 1 to 3.

6. The composition according to claim 1, which additionally comprises at least one radically polymerizable monomer and at least one initiator for the radical polymerization.

7. The composition according to claim 6, in which the radically polymerizable monomer is a mono- or multifunctional (meth)acrylate, or a di(meth)acrylate or a mixture of mono- and multifunctional (meth)acrylates.

8. The composition according to claim 6, which comprises, as additional monomer, methyl, butyl, tetrahydrofurfuryl or isobornyl (meth)acrylate, p-cumylphenoxyethylene glycol methacrylate (CMP-1E), bisphenol A di(meth)acrylate, 2-[4-(2-(meth)acryloyloxyethoxyethoxy)phenyl]-2-[4-(2-methacryloyl-oxyethoxy)phenyl]-propane), 1,6-bis-[2-(meth)acryloyloxyethoxycarbonylamino]-2,2,4-trimethylhexane (UD(M)A); tri- or tetraethylene glycol di(meth)acrylate, glycerol tri(meth)acrylate, 1,10-decanediol di(meth)acrylate ($D_3$MA), 1,12-dodecanediol di(meth)acrylate or a mixture thereof.

9. The composition according to claim 1, which additionally comprises at least one inorganic filler.

10. The composition according to claim 1, which comprises
a) 0.1 to 30 wt.-% of at least one compound according to general formula I,
b) 0.01 to 5 wt.-% at least one initiator for the radical polymerization,
c) 1 to 90 wt.-% of at least one mono- or multifunctional (meth)acrylate,
d) 0 to 85 wt.-% of at least one filler, in each case relative to the total mass of the composition.

11. The composition according to one of claim 1 for intraoral use for the restoration of damaged teeth.

12. The composition according to claim 1 for use as a medical material for the production of medical products for surgery comprising a material for the production of implants for hearing prostheses, cartilage or bone replacements, or a material for the production of intraocular lenses.

13. The composition according to claim 1, in which the variables of Formula I have the following meanings:

A H, CN, a cycloaliphatic, linear or branched aliphatic $C_1$-$C_{30}$ hydrocarbon residue, which can be substituted by 1 to 6 substituents comprising —$CH_3$, —$C_2H_5$, —OH, —$OCH_3$ and/or —O—$COCH_3$, which can be interrupted by 1 to 4 urethane groups, ester groups, O and/or S and which can contain 1 or 2 benzene groups, an aromatic $C_6$-$C_{30}$ hydrocarbon residue, which can be substituted by 1 to 6 substituents comprising —$CH_3$, —$C_2H_5$, —OH, —$OCH_3$ and/or —O—$COCH_3$, or a combination thereof, wherein the hydrocarbon residues can bear a polymerizable group terminally;

X is dispensed with when A is an aromatic hydrocarbon residue or CN;

B H, CN, a cycloaliphatic, linear or branched aliphatic $C_1$-$C_{30}$ hydrocarbon residue, which can be substituted by 1 to 6 substituents comprising —$CH_3$, —$C_2H_5$, —OH, —$OCH_3$ and/or —O—$COCH_3$, which can be interrupted by 1 to 4 urethane groups, ester groups, O and/or S and which can contain 1 or 2 benzene groups, an aromatic $C_6$-$C_{30}$ hydrocarbon residue, which can be substituted by 1 to 6 substituents comprising —$CH_3$, —$C_2H_5$, —OH, —$OCH_3$ and/or —O—$COCH_3$, or a combination thereof, wherein the hydrocarbon residues can bear a polymerizable group terminally;

Y is dispensed with when B is an aromatic hydrocarbon residue or CN;

$R^{1-3}$ in each case independently of one another hydrogen, a cycloaliphatic, linear or branched aliphatic $C_1$-$C_{10}$ hydrocarbon residue, which can be interrupted by 1 to 4 oxygen atoms and which can be substituted by 1 to 4 OH groups, or an aromatic $C_6$-$C_{10}$ hydrocarbon residue, which can be substituted by 1 to 4, OH groups;

m an integer from 1 to 6;

n an integer from 1 to 6;

p an integer from 1 to 6; wherein m and p cannot be greater than 1 at the same time and wherein if m=1, p=n, and if p=1, m=n.

14. The composition according to claim 2, in which the variables of Formula II have the following meanings:

A H, CN, a cycloaliphatic, linear or branched aliphatic $C_1$-$C_{30}$ hydrocarbon residue, which can be substituted by 1 to 6 substituents comprising —$CH_3$, —$C_2H_5$, —OH, —$OCH_3$ and/or —O—$COCH_3$, which can be interrupted by 1 to 4 urethane groups, ester groups, O and/or S and which can contain 1 or 2 benzene groups, an aromatic $C_6$-$C_{30}$ hydrocarbon residue, which can be substituted by 1 to 6 substituents comprising —$CH_3$, —$C_2H_5$, —OH, —$OCH_3$ and/or —O—$COCH_3$, or a combination thereof, wherein the hydrocarbon residues can bear a polymerizable group terminally;

X is preferably dispensed with when A is an aromatic hydrocarbon residue or CN;

B H, CN, a cycloaliphatic, linear or branched aliphatic $C_1$-$C_{30}$ hydrocarbon residue, which can be substituted by 1 to substituents comprising —$CH_3$, —$C_2H_5$, —OH, —$OCH_3$ and/or —O—$COCH_3$, which can be interrupted by 1 to 4 urethane groups, ester groups, O and/or S and which can contain 1 or 2 benzene groups, an aromatic $C_6$-$C_{30}$ hydrocarbon residue, which can be substituted by 1 to 6 substituents comprising —$CH_3$, —$C_2H_5$, —OH, —$OCH_3$ and/or —O—$COCH_3$, or a combination thereof, wherein the hydrocarbon residues can bear a polymerizable group terminally;

Y is dispensed with when B is an aromatic hydrocarbon residue or CN;

$R^{1-3}$ in each case independently of one another hydrogen, a cycloaliphatic, linear or branched aliphatic $C_1$-$C_{10}$ hydrocarbon residue, which can be interrupted by 1 to 4 oxygen atoms and which can be substituted by 1 to 4 OH groups, or an aromatic $C_6$-$C_{10}$ hydrocarbon residue, which can be substituted by 1 to 4 OH groups;

n an integer from 1 to 6.

15. The composition according to claim 3, in which the variables of Formula II have the following meanings:

A cycloaliphatic, linear or branched aliphatic $C_1$-$C_{12}$ hydrocarbon residue, which can be substituted by 1 to 3 substituents comprising —$CH_3$, —$C_2H_5$, —OH and/or —$OCH_3$, which can be interrupted by 1 to 2 urethane groups, ester groups, O and/or S and which can contain 1 to 2 1,4-phenylene groups, an aromatic $C_6$-$C_{14}$ hydrocarbon residue, which can be substituted by 1 to 3 substituents comprising —$CH_3$, —$C_2H_5$, —OH, —$OCH_3$ and/or —O—$COCH_3$, or a combination thereof, wherein the hydrocarbon residues can bear a (meth)acrylate group, terminally;

X is dispensed with when A is an aromatic hydrocarbon residue;

B cycloaliphatic, linear or branched aliphatic $C_1$-$C_{12}$ hydrocarbon residue, which can be interrupted by 1 to 2 urethane groups, ester groups, O and/or S and which can contain 1 to 2 1,4-phenylene groups, an aromatic $C_6$-$C_{14}$ hydrocarbon residue, which can be substituted by 1 to 3 substituents comprising —$CH_3$, —$C_2H_5$, —OH, —$OCH_3$ and/or —O—$COCH_3$, or a combination thereof, wherein the hydrocarbon residues can bear a polymerizable (meth)acrylate group, terminally;

Y is dispensed with when B is an aromatic hydrocarbon residue;

$R^{1-3}$ in each case independently of one another hydrogen, a cycloaliphatic, linear or branched aliphatic $C_1$-$C_6$ hydrocarbon residue, which can be interrupted by 1 to 2 oxygen atoms and which can be substituted by 1 to 2 OH groups, or an aromatic $C_6$-$C_{10}$ hydrocarbon residue, which can be substituted by 1 to 2 OH groups;

n an integer from 1 to 3.

16. The composition according to claim 4, in which the variables of Formula III have the following meanings:

A H, CN, a cycloaliphatic, linear or branched aliphatic $C_1$-$C_{30}$ hydrocarbon residue, which can be substituted by 1 to 6 substituents comprising —$CH_3$, —$C_2H_5$, —OH, —$OCH_3$ and/or —O—$COCH_3$, which can be interrupted by 1 to 4, urethane groups, ester groups, O and/or S and which can contain 1 or 2 benzene groups, an aromatic $C_6$-$C_{30}$ hydrocarbon residue, which can be substituted by 1 to 6 substituents comprising —$CH_3$, —$C_2H_5$, —OH, —$OCH_3$ and/or —O—$COCH_3$, or a combination thereof, wherein the hydrocarbon residues can bear a polymerizable group terminally;

X is dispensed with when A is an aromatic hydrocarbon residue or CN;

B H, CN, a cycloaliphatic, linear or branched aliphatic $C_1$-$C_{30}$ hydrocarbon residue, which can be substituted by 1 to 6 substituents comprising —$CH_3$, —$C_2H_5$, —OH, —$OCH_3$ and/or —O—$COCH_3$, which can be interrupted by 1 to 4 urethane groups, ester groups, O and/or S and which can contain 1 or 2 benzene groups, an aromatic $C_6$-$C_{30}$ hydrocarbon residue, which can be substituted by 1 to 6 substituents comprising —$CH_3$, —$C_2H_5$, —OH, —$OCH_3$ and/or —O—$COCH_3$, or a combination thereof, wherein the hydrocarbon residues can bear a polymerizable group terminally;

Y is dispensed with when B is an aromatic hydrocarbon residue or CN;

$R^{1-3}$ in each case independently of one another hydrogen, a cycloaliphatic, linear or branched aliphatic $C_1$-$C_{10}$ hydrocarbon residue, which can be interrupted by 1 to 4 oxygen atoms and which can be substituted by 1 to 4 OH groups, or an aromatic $C_6$-$C_{10}$ hydrocarbon residue, which can be substituted by 1 to 4 OH groups;

n an integer from 1 to 6.

17. The composition according to claim 5, in which the variables of Formula III have the following meanings:

A cycloaliphatic, linear or branched aliphatic $C_1$-$C_{12}$ hydrocarbon residue, which can be substituted by 1 to 3 substituents comprising preferably —$CH_3$, —$C_2H_5$, —OH and/or —$OCH_3$, which can be interrupted by 1 to 2 urethane groups, ester groups, O and/or S and which can contain 1 to 2 1,4-phenylene groups, an aromatic $C_6$-$C_{14}$ hydrocarbon residue, which can be substituted by 1 to 3 substituents comprising —$CH_3$, —$C_2H_5$, —OH, —$OCH_3$ and/or —O—$COCH_3$, or a combination thereof, wherein the hydrocarbon residues can bear a (meth)acrylate group, terminally;

X is dispensed with when A is an aromatic hydrocarbon residue;

B cycloaliphatic, linear or branched aliphatic $C_1$-$C_{12}$ hydrocarbon residue, which can be interrupted by 1 to 2 urethane groups, ester groups, O and/or S and which can contain 1 to 2 1,4-phenylene groups, an aromatic $C_6$-$C_{14}$ hydrocarbon residue, which can be substituted by 1 to 3 substituents comprising —$CH_3$, —$C_2H_5$, —OH, —$OCH_3$ and/or —O—$COCH_3$, or a combination thereof, wherein the hydrocarbon residues can bear a (meth)acrylate group, terminally;

Y is dispensed with when B is an aromatic hydrocarbon residue;

$R^{1-3}$ in each case independently of one another hydrogen, a cycloaliphatic, linear or branched aliphatic $C_1$-$C_6$ hydrocarbon residue, which can be interrupted by 1 to 2 oxygen atoms and which can be substituted by 1 to 2 OH groups, or an aromatic $C_6$-$C_{10}$ hydrocarbon residue, which can be substituted by 1 to 2 OH groups;

n an integer from 1 to 3.

18. The composition according to claim 10, which comprises
a) 1 to 25 wt.-% of at least one compound according to general formula I,
b) 0.1 to 3.0 wt.-% of at least one initiator for the radical polymerization,
c) 1 to 80 wt.-% of at least one mono- or multifunctional (meth)acrylate,
d) 0 to 80 wt.-% of at least one filler, in each case relative to the total mass of the composition.

19. The composition according to claim 10, which comprises
a) 1 to 15 wt.-% of at least one compound according to general formula I, b) 0.01 to 5 wt.-% of at least one initiator for the radical polymerization,
c) 10 to 80 wt.-% of at least one mono- or multifunctional (meth)acrylate,
d) 0 to 75 wt.-% of at least one filler, in each case relative to the total mass of the composition.

\* \* \* \* \*